(12) United States Patent
Lu

(10) Patent No.: US 9,655,965 B2
(45) Date of Patent: May 23, 2017

(54) RADIOSENSITIZER COMPOUNDS FOR USE IN COMBINATION WITH RADIATION

(71) Applicant: Qing-Bin Lu, Waterloo (CA)

(72) Inventor: Qing-Bin Lu, Waterloo (CA)

( * ) Notice: Subject to any disclaimer, the term of this patent is extended or adjusted under 35 U.S.C. 154(b) by 0 days.

(21) Appl. No.: 14/654,165

(22) PCT Filed: Dec. 20, 2013

(86) PCT No.: PCT/CA2013/051005
§ 371 (c)(1),
(2) Date: Jun. 19, 2015

(87) PCT Pub. No.: WO2014/094178
PCT Pub. Date: Jun. 26, 2014

(65) Prior Publication Data
US 2015/0343059 A1    Dec. 3, 2015

(51) Int. Cl.
| | | |
|---|---|---|
| *A61K 31/136* | (2006.01) | |
| *A61K 31/44* | (2006.01) | |
| *A61K 31/4965* | (2006.01) | |
| *A61K 41/00* | (2006.01) | |
| *C07D 213/73* | (2006.01) | |
| *C07C 211/52* | (2006.01) | |
| *C07D 241/20* | (2006.01) | |
| *A61N 5/10* | (2006.01) | |

(52) U.S. Cl.
CPC ........ *A61K 41/0038* (2013.01); *A61K 31/136* (2013.01); *A61K 31/44* (2013.01); *A61K 31/4965* (2013.01); *C07C 211/52* (2013.01); *C07D 213/73* (2013.01); *C07D 241/20* (2013.01); *A61N 2005/1098* (2013.01)

(58) Field of Classification Search
CPC .. A61K 31/136; A61K 31/44; A61K 31/4965; A61K 41/0038
See application file for complete search history.

(56) References Cited

FOREIGN PATENT DOCUMENTS

| CA | 2603810 C | 10/2006 |
|---|---|---|
| WO | 2006/067466 A2 | 6/2006 |
| WO | 2008/082487 A2 | 7/2008 |

OTHER PUBLICATIONS

International Search Report for application No. PCT/CA2013/051005, dated Mar. 11, 2014 (7 pages).
Written Opinion of the International Searching Authority for application No. PCT/CA2013/051005, dated Mar. 11, 2014 (9 pages).
International Preliminary Report on Patentability for application No. PCT/CA2013/051005, dated Jun. 23, 2015. (10 pages).
Chemical Abstracts Service—Registry No. (Entry Date): 1219741-20-4 (2010).
Chemical Abstracts Service—Registry No. (Entry Date): 857439-62-4 (2005).
Chemical Abstracts Service—Registry No. (Entry Date): 76179-43-6 (1984).
Chemical Abstracts Service—Registry No. (Entry Date): 75293-95-7 (1984).
Chemical Abstracts Service—Registry No. (Entry Date): 72435-64-4 (1984).
Chemical Abstracts Service—Registry No. (Entry Date): 49764-63-8 (1984).
Chemical Abstracts Service—Registry No. (Entry Date): 5348-42-5 (1984).
Chemical Abstracts Service—Registry No. (Entry Date): 927696-05-7 (2007).
Chemical Abstracts Service—Registry No. (Entry Date): 858241-27-7 (2005).
Chemical Abstracts Service—Registry No. (Entry Date): 182631-88-5 (1996).
Chemical Abstracts Service—Registry No. (Entry Date): 78582-07-7 (1984).
Chemical Abstracts Service—Registry No. (Entry Date): 68459-98-3 (1984).
Chemical Abstracts Service—Registry No. (Entry Date): 57803-83-5 (1984).
Chemical Abstracts Service—Registry No. (Entry Date): 33848-51-0 (1984).
Chemical Abstracts Service—Registry No. (Entry Date): 33848-50-9 (1984).
Chemical Abstracts Service—Registry No. (Entry Date): 33087-39-7 (1984).
Chemical Abstracts Service—Registry No. (Entry Date): 21537-34-8 (1984).
Chemical Abstracts Service—Registry No. (Entry Date): 21537-33-7 (1984).
Chemical Abstracts Service—Registry No. (Entry Date): 21537-32-6 (1984).
Chemical Abstracts Service—Registry No. (Entry Date): 21304-38-1 (1984).
Chemical Abstracts Service—Registry No. (Entry Date): 1575-37-7 (1984).
Chemical Abstracts Service—Registry No. (Entry Date): 95-83-0 (1984).

(Continued)

*Primary Examiner* — James D Anderson
(74) *Attorney, Agent, or Firm* — Brian C. Trinque; Lathrop & Gage LLP

(57) ABSTRACT

Disclosed herein are radiosensitizer compounds useful in combination with radiation therapy, e.g., a synergistic combination therapy for the treatment of cancer and other disorders. The radiosensitizer compounds have the general formula I: wherein A represents an aromatic core; at least one of $R^a$ and $R^b$ is an electron transfer promoter as defined herein, e.g., $NH_2$; and at least one of $R^c$ is a leaving group as defined herein, e.g., halogen; and the remainder of the molecule is as defined herein. Pharmaceutical compositions, methods, uses, kits and commercial packages comprising the radiosensitizer compounds are also disclosed.

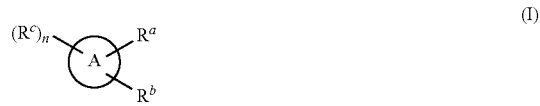

20 Claims, 30 Drawing Sheets

(56) References Cited

OTHER PUBLICATIONS

Chemical Abstracts Service—Registry No. (Entry Date): 1394373-23-9 (2012).
Chemical Abstracts Service—Registry No. (Entry Date): 1195519-49-3 (2009).
Chemical Abstracts Service—Registry No. (Entry Date): 97941-89-4 (1985).
Chemical Abstracts Service—Registry No. (Entry Date): 1254171-36-2 (2010).
Chemical Abstracts Service—Registry No. (Entry Date): 1241725-95-0 (2010).
Chemical Abstracts Service—Registry No. (Entry Date): 1215698-73-9 (2010).
Chemical Abstracts Service—Registry No. (Entry Date): 1171836-31-9 (2009).
Chemical Abstracts Service—Registry No. (Entry Date): 426463-01-6 (2002).
Chemical Abstracts Service—Registry No. (Entry Date): 351447-14-8 (2001).
Chemical Abstracts Service—Registry No. (Entry Date): 129012-04-0 (1990).
Chemical Abstracts Service—Registry No. (Entry Date): 40851-95-4 (1984).
Chemical Abstracts Service—Registry No. (Entry Date): 40851-88-5 (1984).
Chemical Abstracts Service—Registry No. (Entry Date): 38875-53-5 (1984).
Chemical Abstracts Service—Registry No. (Entry Date): 25710-20-7 (1984).
Chemical Abstracts Service—Registry No. (Entry Date): 53338-46-8 (1984).
Chemical Abstracts Service—Registry No. (Entry Date): 13484-57-6 (1984).
Chemical Abstracts Service—Registry No. (Entry Date): 1259479-81-6 (2011).
Chemical Abstracts Service—Registry No. (Entry Date): 89123-58-0 (1984).

A

B

C

D

E

F

G

H

I

J

K

L

Electrolyte Profile (0mg/kg Compound B)

Electrolyte Profile (5mg/kg Compound B)

Electrolyte Profile (7mg/kg Compound B)

RADIOSENSITIZER COMPOUNDS FOR USE IN COMBINATION WITH RADIATION

CROSS-REFERENCE TO RELATED APPLICATIONS

Related Applications

This application is a 35 U.S.C. §371 filing of International Application No. PCT/CA2013/051005, filed Dec. 20, 2013, which claims priority to U.S. Patent Application No. 61/797,983, filed Dec. 20, 2012, both of which are incorporated herein by reference in their entireties.

BACKGROUND

Cancer is a major health problem across the globe. Current treatments generally involve surgery, radiation therapy (radiotherapy), chemotherapy, or a combination of these approaches, each of which has limitations. There remains a need for new and improved cancer therapies, including combination therapies.

It is estimated that approximately two thirds of cancer patients receive radiotherapy, which involves the application of ionizing radiation as part of a treatment to control or kill malignant cells. Ionizing radiation is used to damage the DNA of exposed tissue leading to cell death. Radiotherapy may be curative in a number of types of cancer. It may also be used as part of adjuvant therapy, to prevent tumor recurrence after surgical removal. Radiotherapy may be synergistic with chemotherapy, and has been used before, during, and after chemotherapy in susceptible cancers. Many common cancer types can be treated with radiation therapy in some way. The precise treatment intent will depend on the tumor type, location, stage, and health of the patient. Radiotherapy also has applications in non-malignant conditions, such as the treatment of trigeminal neuralgia, acoustic neuromas, severe thyroid eye disease, pterygium, pigmented villonodular synovitis, and prevention of keloid scar growth, vascular restenosis, and heterotopic ossification.

Exposure of living cells to ionizing radiation leads to biological damage by both direct and indirect interactions with cell components, mainly DNA. The direct action of radiation, e.g. direct energy deposited in the DNA, accounts for only a small fraction of the energy deposited into the biological system. The cell contains 70-80% water. It is known that the contribution of free radicals, via radiolysis of water, to biological damage far exceeds that of direct action in ionizing radiation, by orders of magnitude.

Different cancers respond differently to radiotherapy. The response of a cancer to radiation is described by its radiosensitivity. Highly radiosensitive cancer cells are rapidly killed by modest doses of radiation. These include leukemias, most lymphomas and germ cell tumors. Most of the epithelial cancers are only moderately radiosensitive, and require a significantly higher dose of radiation (60-70 Gy) to achieve a radical cure. Some types of cancer, such as renal cell cancer and melanoma, are highly radioresistant and cannot be cured by radiation doses that are safe in clinical practice. The response of a tumor to radiotherapy is also related to its size and conditions. For complex reasons, very large tumors respond less well to radiation than smaller tumors or microscopic disease. One technique to enhance the radiosensitivity of a cancer is by giving a radiosensitizing drug (a so-called "radiosensitizer") during a course of radiotherapy.

Radiotherapy itself is painless, but it can cause serious side effects. Particularly high doses can cause varying side effects, including acute side effects happening in the months following treatment, long-term side effects in years following treatment, and cumulative side effects after re-treatment. The nature, severity, and longevity of side effects depends on the organs that receive the radiation, the treatment itself (type of radiation, dose, fractionation, concurrent chemotherapy), and the patient. Acute side effects include fatigue and skin irritation, nausea and vomiting, damage to the epithelial surfaces, mouth, throat and stomach sores, intestinal discomfort, swelling (edema) and infertility. In clinical oncology, efforts are made to use low radiation doses to reduce toxic side effects, e.g., by use of a radiosensitizer to enhance the treatment efficacy.

Cisplatin (cis-Pt(NH3)$_2$Cl$_2$) is a platinum-based antineoplastic drug and is one of the most widely used drugs for cancer treatment. Cisplatin has also been used as a radiosensitizer to enhance the radiosensitivity of the cancer during radiotherapy [Rose et al., 1999]. Despite its widespread use, cisplatin has two major drawbacks: severe toxic side effects and both intrinsic and acquired resistance. These drawbacks even led to the calling of terminating the clinical applications of the heavy-metal Pt-based anticancer drugs [Reese, 1995]. There remains a need to identify less toxic analogues and to develop combination therapies, including chemo-radiotherapies, that reduce cisplatin toxicity and prevent or overcome drug resistance.

While a variety of chemotherapeutic agents have been combined with radiotherapy, nearly all are toxic. Chemotherapeutic agents generally cause significant, and often dangerous, side effects. Side effects associated with chemotherapeutic agents are generally the major factor in defining a dose-limiting toxicity (DLT) for the agent.

WO/2011/026219 (to the present inventor), entitled Combination Therapy for Cancer Comprising a Platinum-Based Antineoplastic Agent and a Biocompatible Electron Donor, there is disclosed a combination chemotherapy of cisplatin with an electron-donating agent to enhance the anti-cancer efficacy of cisplatin (also see, Lu, 2011).

SUMMARY OF THE INVENTION

Generally, the present disclosure relates to non-platinum-based radiosensitizer compounds for use in combination with radiation therapy, e.g. to enhance radiotherapy.

Accordingly, the present disclosure also relates to a combination therapy for cancer and other disorders treatable by radiation therapy. Also disclosed herein are compositions, dosage forms, methods, uses, commercial packages and kits relating to the compounds.

In one aspect, there is provided a radiosensitizer compound useful in combination with radiation, having the general formula I:

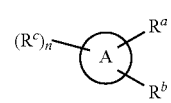

(I)

wherein A represents an aromatic core; at least one of $R^a$ and $R^b$ is an electron transfer promoter as defined herein; and at least one of $R^c$ is a leaving group as defined herein.

In one aspect, the biocompatible radiosensitizer compound for use in combination with ionizing radiation has the general formula I:

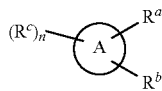
(I)

wherein A is a 5- or 6-membered aryl or heteroaryl ring containing 0-2 ring heteroatoms selected from the group consisting of N, O and S, the remaining ring atoms being carbon; $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of $R^a$ and $R^b$ is an electron transfer promoter; $R^c$ is, independently for each occurrence, H, OH, alkyl, alkoxy, alkenyl, alkynyl, cycloalkyl, cycloalkenyl, cycloalkynyl, aryl, heterocyclyl, heteroaryl, or a leaving group, or two adjacent $R^c$ groups taken together with the ring atoms to which they are attached form a 5- or 6-membered saturated, partially saturated or unsaturated ring which contains 0-2 ring heteroatoms selected from N, O and S and which can be optionally substituted with 1-4 $R^d$; wherein at least one $R^c$ is a leaving group; $R^d$ is independently OH, alkyl, alkoxy, alkenyl, alkynyl, cycloalkyl, cycloalkenyl, cycloalkynyl, aryl, heterocyclyl or heteroaryl; and n=1-4, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In another aspect, there is provided radiosensitizer compound having the general formula II:

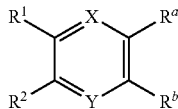
(II)

wherein: X and Y are independently C—$R^3$ or N; $R^3$ is H, OH, halogen, alkyl, alkoxy, alkenyl, alkynyl, cycloalkyl, cycloalkenyl, cycloalkynyl, aryl, heterocyclyl, or heteroaryl; $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of $R^a$ and $R^b$ is an electron transfer promoter; $R^1$ and $R^2$ are, independently, H, OH, alkyl, alkoxy, alkenyl, alkynyl, cycloalkyl, cycloalkenyl, cycloalkynyl, aryl, heterocyclyl, heteroaryl, or a leaving group; wherein at least one of $R^1$ and $R^2$ is a leaving group, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In another aspect, there is provided a compound having the general formula III,

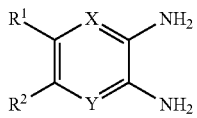
(III)

wherein X and Y are independently C—$R^3$ or N; $R^3$ is H, OH, halogen, alkyl, alkoxy, alkenyl, alkynyl, cycloalkyl, cycloalkenyl, cycloalkynyl, aryl, heterocyclyl, or heteroaryl; $R^1$ and $R^2$ are, independently, H, OH, alkyl, alkoxy, alkenyl, alkynyl, cycloalkyl, cycloalkenyl, cycloalkynyl, aryl, heterocyclyl, heteroaryl, or a leaving group; wherein at least one of $R^1$ and $R^2$ is a leaving group, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In some embodiments of Formula I or II, each of $R^a$ and $R^b$ is an electron transfer promoter. In some embodiments described herein, the electron transfer promoter is selected from the group consisting of —$NH_2$, —NHR, —$NR_2$, —OH, —$NHCOCH_3$, —NHCOR, —$OCH_3$, and —OR. In some embodiments, the electron transfer promoter is —$NH_2$, —NHR, or —$NR_2$. In some embodiments, R is substituted or unsubstituted alkyl. In some embodiments, $R^a$ and $R^b$ are each electron transfer promoters. In some embodiments, $R^a$ and $R^b$ are on adjacent ring carbon atoms. In some embodiments, the electron transfer promoter is —$NH_2$.

In some embodiments, the leaving group is halogen. In some embodiments, the halogen is Cl, Br or I. In some embodiments of Formula I, two $R^c$ groups on Ring A are halogen selected from the group consisting of Cl, Br and I.

In some embodiments of Formula I, Ring A is a 6-membered aryl or heteroaryl ring, such as, benzene, pyridine or pyrazine. In some embodiments Ring A is benzene.

In some embodiments of Formula I, Ring A is benzene, pyridine or pyrazine; each of $R^a$ and $R^b$ are $NH_2$; two $R^c$ substituents on Ring A are halogen each positioned meta to $R^a$ and $R^b$ on Ring A; and any remaining $R^c$ groups are as defined herein. In some embodiments, Ring A is benzene and, in some further embodiments, the remaining carbons on Ring A are unsubstituted carbon. In some embodiments, Ring A is pyridine and, in further embodiments, the remaining carbon on Ring A is unsubstituted. In some embodiments, Ring A is pyrazine.

In some embodiments of Formula II or III, $R^1$ and $R^2$ are both leaving groups, such as halogen. In some embodiments, each halogen is selected from the group consisting of Cl, Br and I.

In some embodiments of Formula II or III, X and Y are C—$R^3$. In some embodiments of Formula II or III, X is C—$R^3$ and Y is N. In some embodiments, $R^3$ is H, OH, halogen, alkyl, alkoxy, alkenyl, alkynyl, cycloalkyl, cycloalkenyl, cycloalkynyl, aryl, heterocyclyl, or heteroaryl. In some embodiments, where the ring carbon is unsubstituted, R is H. In some embodiments of Formula II or III, X and Y are each N.

In some embodiments, the radiosensitizer compound is a compound selected from the group consisting of:

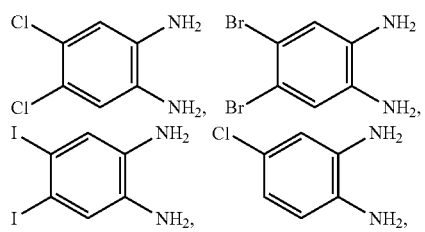

-continued

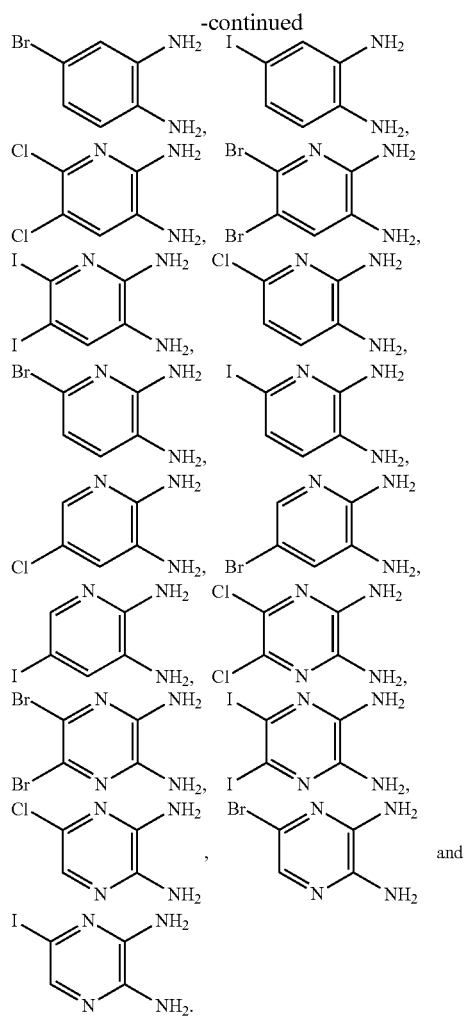

In some embodiments, the radiosensitizer compounds disclosed herein have an electron affinity greater than 0 eV. In some embodiments, the radiosensitizer compounds disclosed herein have an electron affinity between about +0.0 eV to +5 eV. In some embodiments, the radiosensitizer compounds disclosed herein have an electron affinity between about +0.5 eV and about +2.5 eV.

In another aspect, there are provided radiosensitizer compounds as defined herein for enhancing the effects of radiation therapy in a subject receiving said radiation therapy. In some embodiments, the subject is the receiving radiation therapy as a treatment for cancer.

In another aspect, there are provided radiosensitizer compounds as defined herein for for use in the treatment of cancer in a subject receiving radiation therapy.

In another aspect, there are provided radiosensitizer compounds as defined herein for for use in combination with radiation therapy in the treatment of cancer.

In another aspect, there are provided radiosensitizer compounds as defined herein for for use in the manufacture of a medicament for the treatment of cancer in a subject receiving radiation therapy.

In another aspect, there are provided radiosensitizer compounds as defined herein for use in the manufacture of a medicament for use in combination with radiation therapy the treatment of cancer.

In another aspect, there is provided a use of a radiosensitizer compound as defined herein to enhance radiation therapy in a subject receiving said radiation therapy.

In another aspect, there is provided a use of a radiosensitizer compound as defined herein in the treatment of cancer in a subject receiving radiation therapy.

In another aspect, there is provided a use of a radiosensitizer compound as defined herein in the manufacture of a medicament for the treatment of cancer in a subject receiving radiation therapy.

In another aspect, there is provided a pharmaceutical composition for use in combination with ionizing radiation in the treatment of cancer, comprising: an effective amount of a radiosensitizer compound as defined herein; and a pharmaceutically acceptable carrier or diluent.

In another aspect, there is provided combination therapy for cancer comprising a radiosensitizer compound as defined herein and ionizing radiation.

In another aspect, there is provided a method of enhancing radiotherapy in a subject in need thereof comprising: administering an effective amount of a radiosensitizer compound as defined herein to the subject in combination with an effective amount of ionizing radiation.

In another aspect, there is provided method of providing an anti-cancer effect in a cancer cell, comprising: a) administering to the cancer cell an effective amount of a radiosensitizer compound as defined herein; and b) administering to the cancer cell an effective amount of ionizing radiation, wherein a) and b) are administered sequentially or simultaneously to thereby provide the anti-cancer effect. In some embodiments, the anti-cancer effect is killing of the cancer cell. In some embodiments, the cancer cell is a tumour cell.

In another aspect, there is provided a method of treating cancer in a subject in need thereof comprising: a) administering to the subject an effective amount of a radiosensitizer compound as defined herein; and b) administering to the subject an effective amount of ionizing radiation, wherein a) and b) are administered sequentially or simultaneously. In some embodiments, the compound is administered before, during or after administration of the ionizing radiation.

In another aspect, there is provided a method of treating cancer in a subject in need thereof comprising, administering to the subject a therapeutically effective amount of a radiosensitizer compound as defined herein before or simultaneously with an effective amount of ionizing radiation.

In another aspect, there is provided commercial package or kit comprising a radiosensitizer compound as defined herein; and instructions for use in combination with ionizing radiation.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

dibromo-(1,2-)diamino-pyrazine; I: (4,5-)diiodo-(1,2-)diamino-pyrazine; J: bromo-(1,2-)diamino-pyrazine; K: chloro-(1,2-) diamino-pyrazine; L: iodo-(1,2-)diamino-pyrazine.

Figure 1:
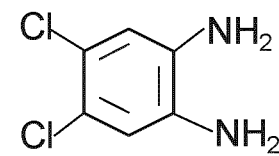
FIG. 1. Molecular structures of 12 exemplary radiosensitizer compounds: A: (4,5-)dichloro-(1,2-)diamino-benzene (4,5-dichloro-1,2-phenylenediamine); B: (4,5-)dibromo-(1,2-)diamino-benzene (4,5-dibromo-1,2-phenylenediamine); C: (4,5-)diiodo-(1,2-)diamino-benzene (4,5-diiodo-1,2-phenylenediamine); D: bromo-(1,2-)diamino-benzene; E: chloro-(1,2-)diamino-benzene; F: iodo-(1,2-)diamino-benzene; G: (4,5-)dichloro-(1,2-) diamino-pyrazine; H: (4,5-)
Figure 1:
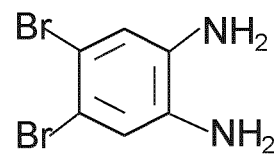
Figure 1:
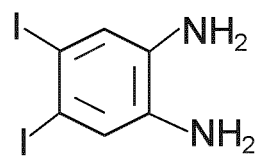
Figure 1:
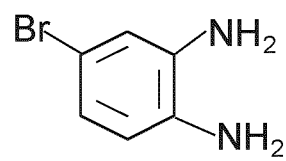
Figure 1:
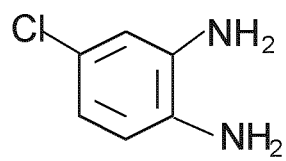
Figure 1:
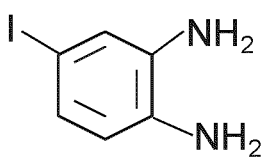
Figure 1:
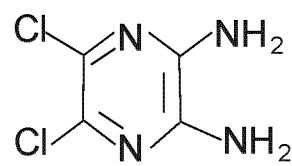
Figure 1:
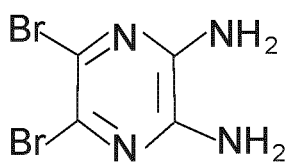
Figure 1:
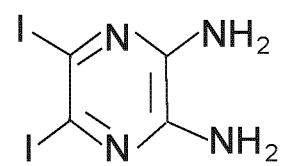
Figure 1:
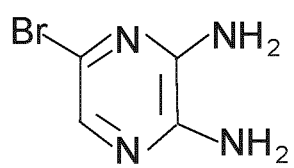
Figure 1:
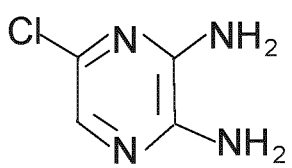
Figure 1:
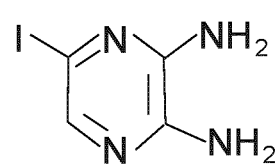
Figure 2:
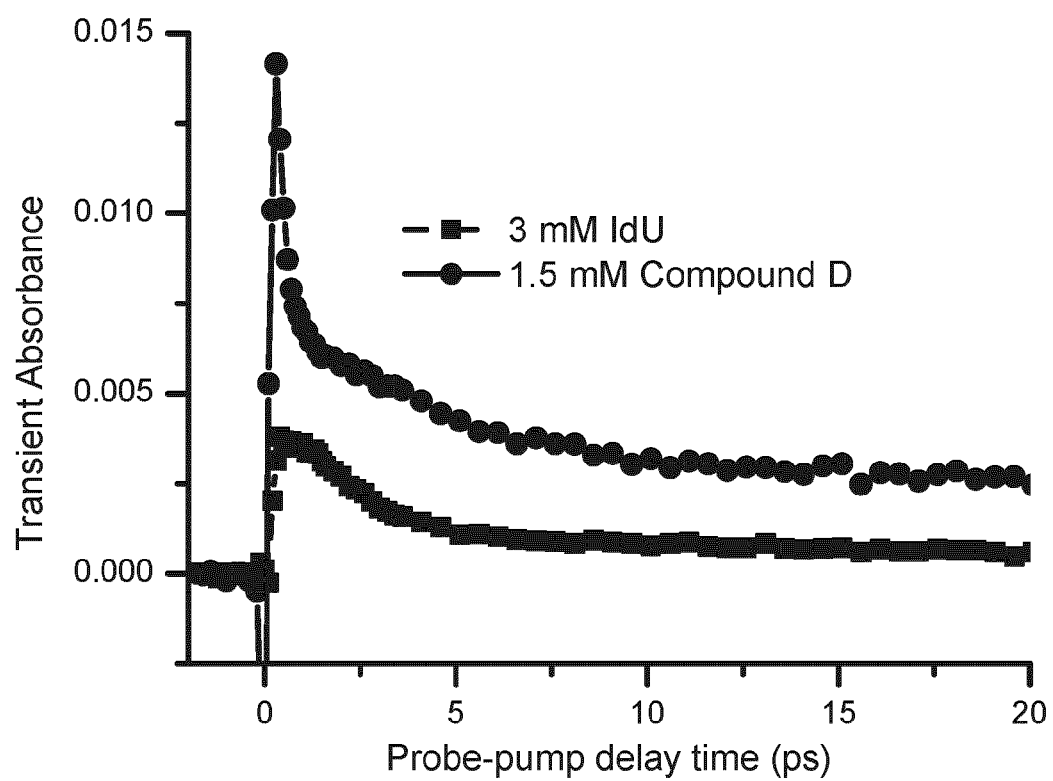

FIG. 2 shows the DET reaction of the prehydrated electron ($e_{pre}^-$) with an exemplary radiosensitizer (compound D), which was observed by fs-TRLS measurements. The results show femtosecond transient absorption kinetic trace of $D^{*-}/IdU^{*-}$ resulting from the DET reaction of $e_{pre}^-$ with compound D or iodopyrimidine (IdU) ($e_{pre}^-$+D/IdU→$D^{*-}$/$IdU^{*-}$→radical formation), pumped at 322 nm and probed at 333 nm in fs-TRLS, showing that the DET reaction efficiency of compound D is much higher than that of IdU. Here $e_{pre}^-$ was generated by two-UV photon excitation of water with the pump pulse. The probe pulse was used to monitor the formation and dissociation of $D^{*-}/IdU^{*-}$.

Figure 3:
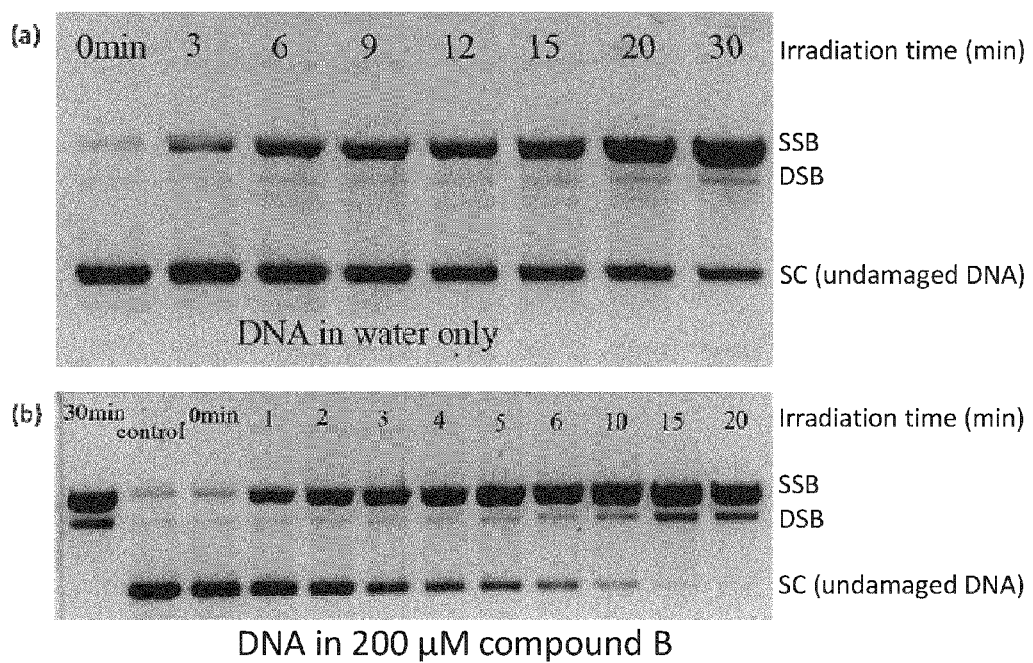

FIG. 3 illustrates the ionizing-radiation-induced damage to plasmid DNA in pure water and with 200 μM Compound B. The damage was measured by agarose gel electrophoresis. Agarose gel electrophoresis images of the ionizing-radiation-induced damage to plasmid DNA in pure water and with 200 μM Compound B, with various durations of a tiny electron source created by two-UV-photon excitation of water in the solution with the power indicated. SC—supercoiled (undamaged DNA); SSB—single-strand breaks; and DSB—double-strand breaks. It is seen that Compound B induced significant enhancement of DSBs.

Figure 4:
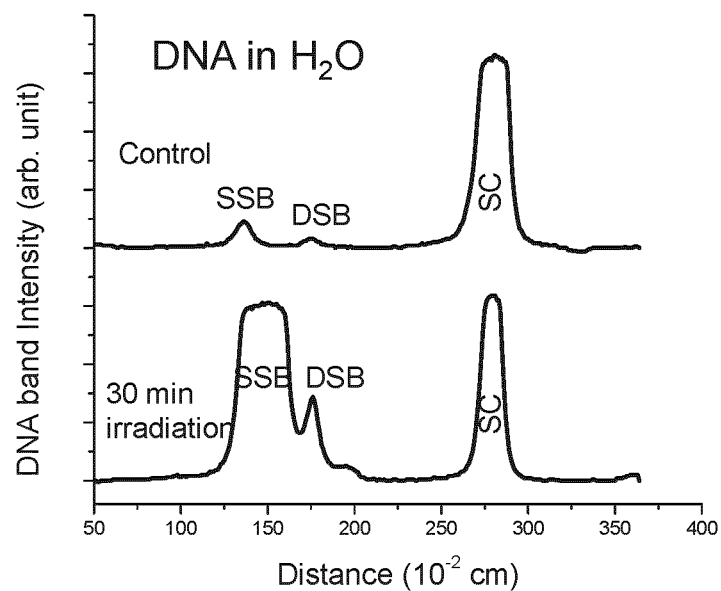
Figure 4:
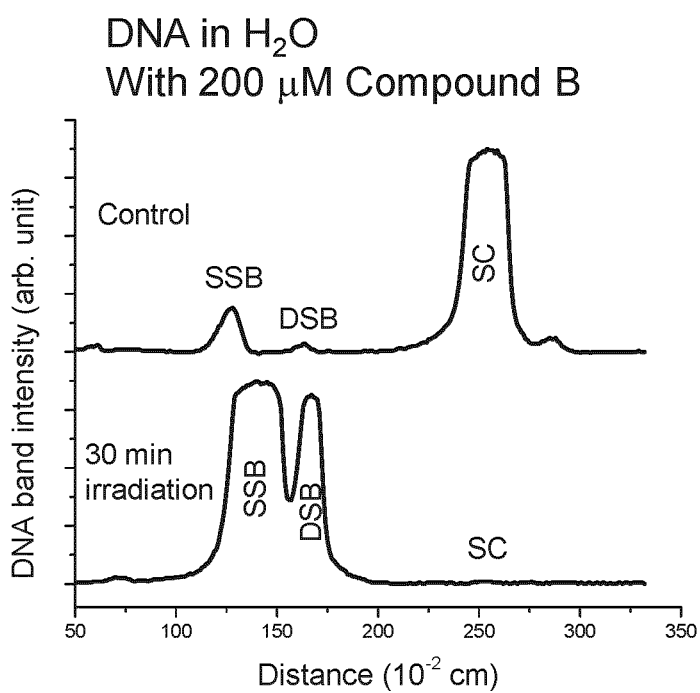

FIG. 4 illustrates the ionizing-radiation-induced damage to plasmid DNA in pure water and with 200 μM Compound B. The damage was analyzed by agarose gel densitograms. Agarose gel densitograms for plasmid DNA in pure water, and 200 μM Compound B, after 30 min 2-photon UV ionizing radiation (see FIG. 3). The results show that Compound B induced significant enhancement of DSBs.

Figure 5:
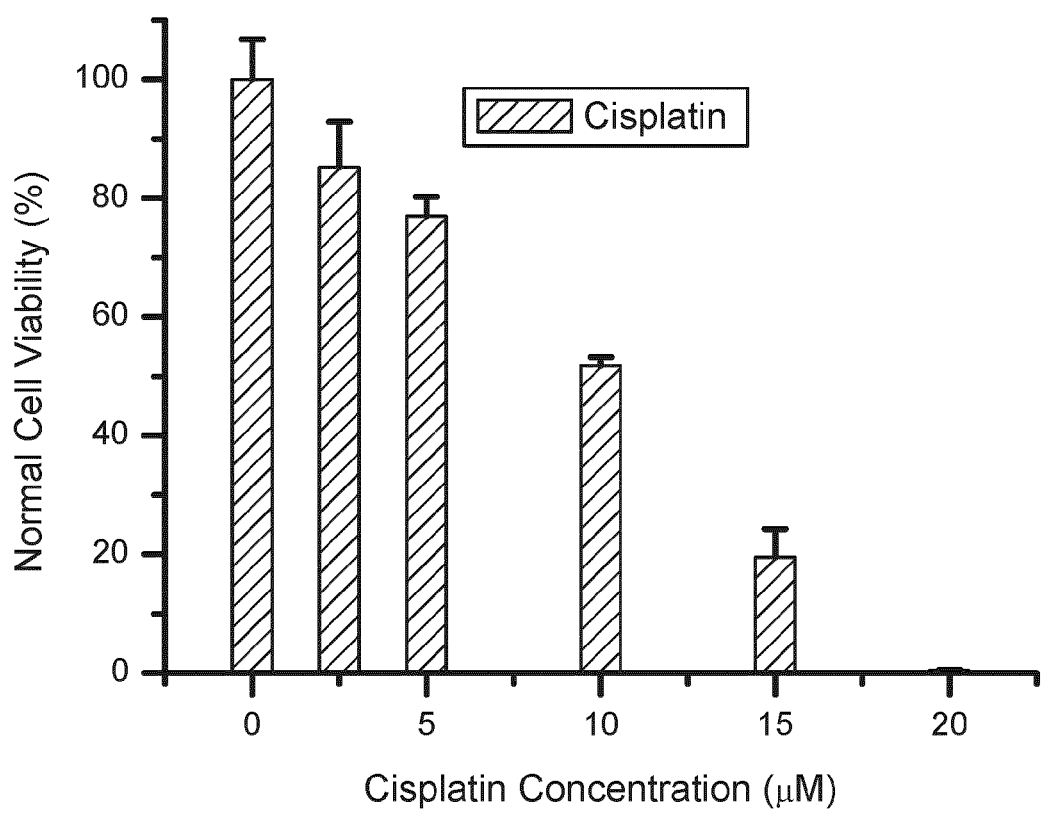

FIG. 5 illustrates cell survival rates of human normal cells (GM05757) after the 72-hr treatment of cisplatin with various concentrations. The viability of cells in 96-well plates was measured by MTT assay. This result confirms that cisplatin itself is highly toxic without ionizing radiation.

Figure 6:
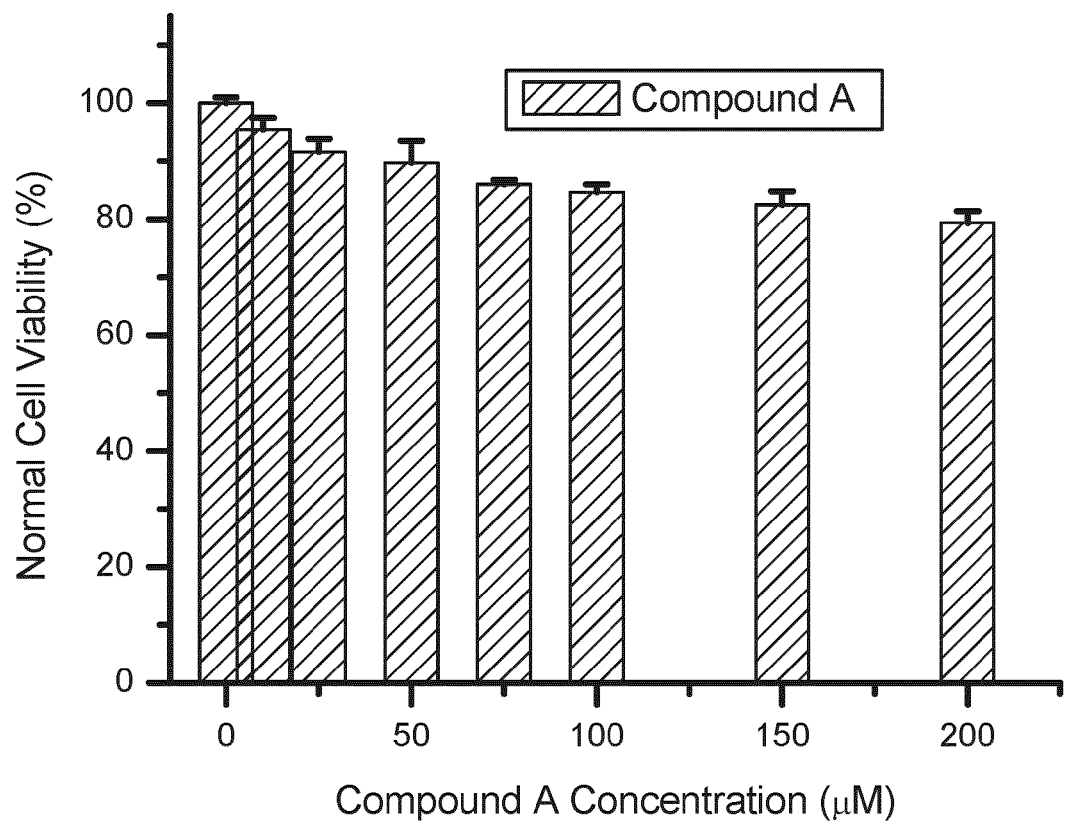

FIG. 6 illustrates cell survival rates of human normal cells (GM05757) after the 72-hr treatment of Compound A with various concentrations. The viability of cells in 96-well plates was measured by MTT assay. This result shows that Compound A itself shows little toxicity up to 200 μM without ionizing radiation.

Figure 7:
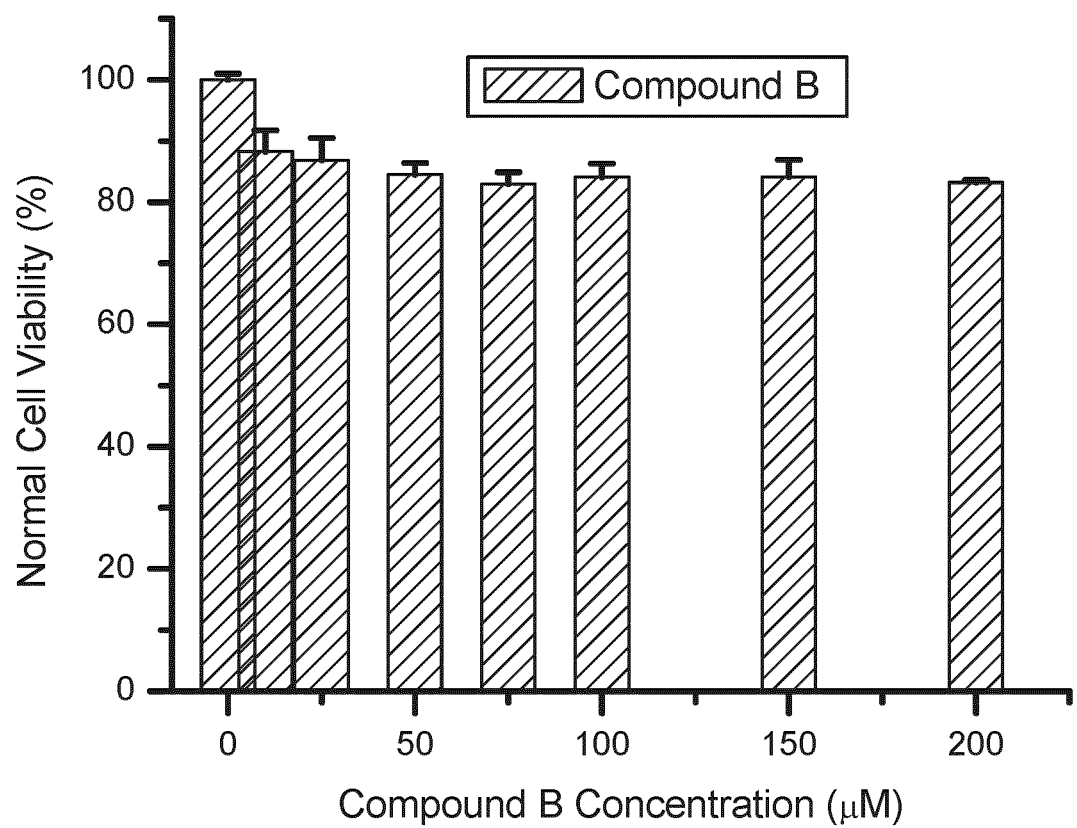

FIG. 7 illustrates cell survival rates of human normal cells (GM05757) after the 72-hr treatment of Compound B with various concentrations. The viability of cells in 96-well plates was measured by MTT assay. This result shows that Compound B itself shows little toxicity up to 200 μM without ionizing radiation.

Figure 8:
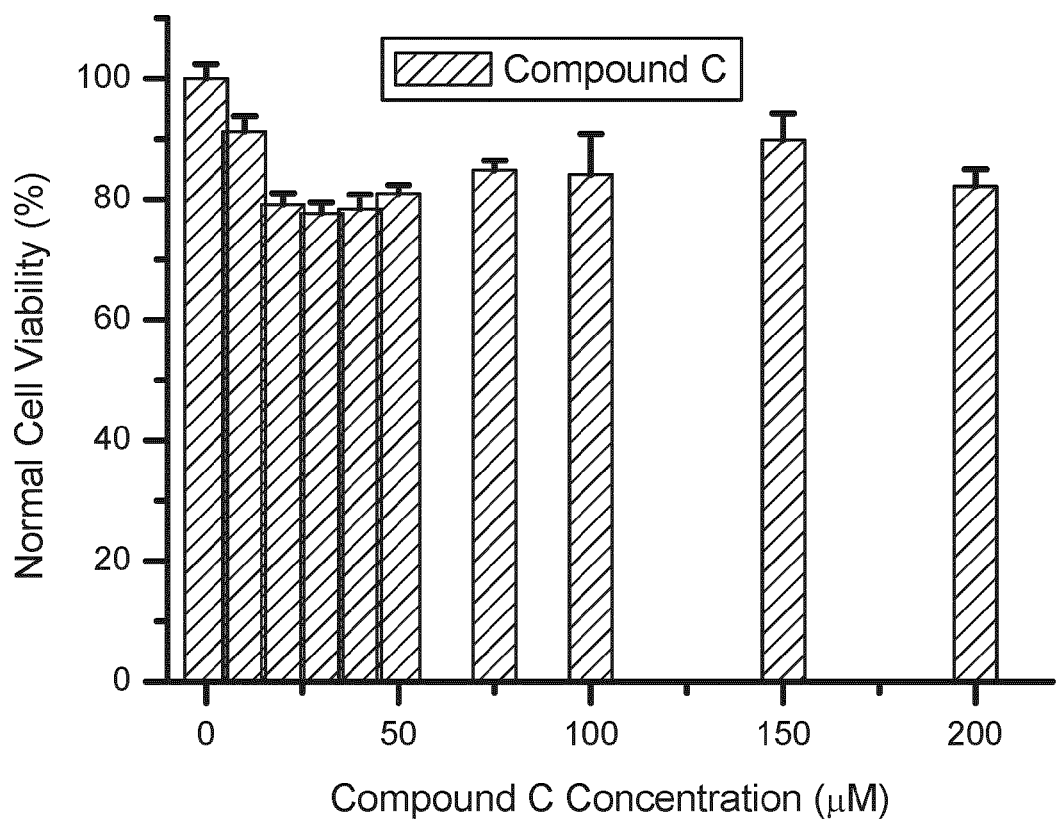

FIG. 8 illustrates cell survival rates of human normal cells (GM05757) after the 72-hr treatment of Compound C with various concentrations. The viability of cells in 96-well plates was measured by MTT assay. This result shows that Compound C itself shows little toxicity up to 200 μM without ionizing radiation.

Figure 9:
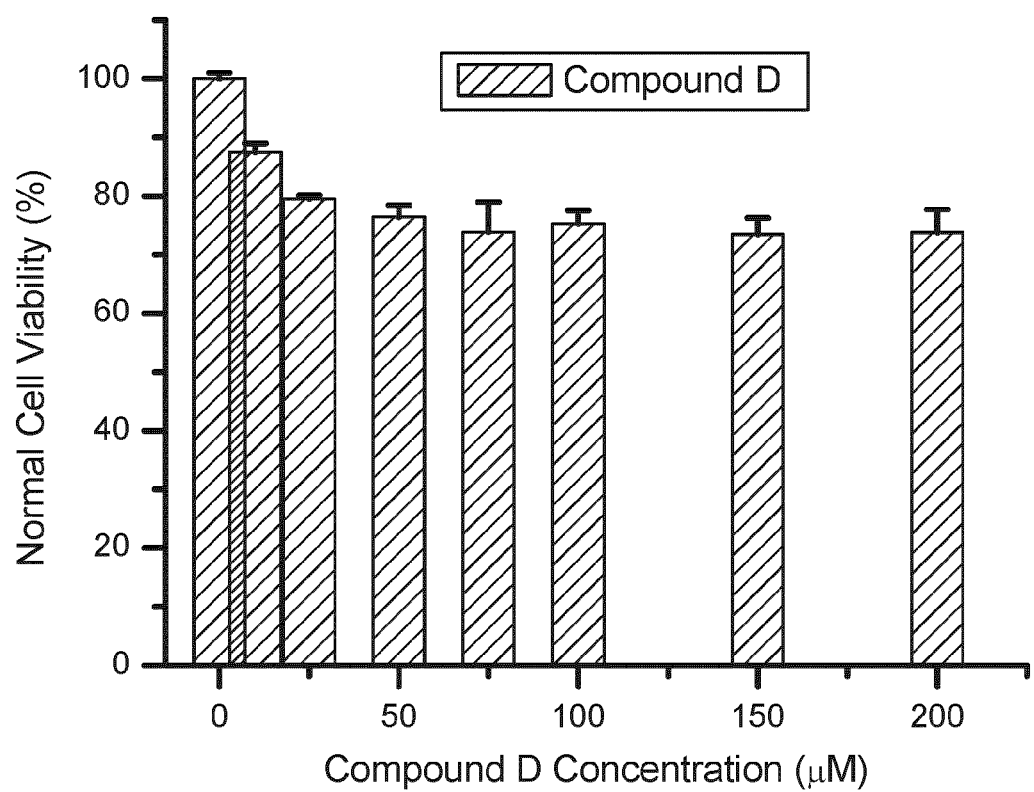

FIG. 9 illustrates cell survival rates of human normal cells (GM05757) after the 72-hr treatment of Compound D with various concentrations. The viability of cells in 96-well plates was measured by MTT assay. This result shows that Compound D itself shows little toxicity up to 200 μM without ionizing radiation.

Figure 10:
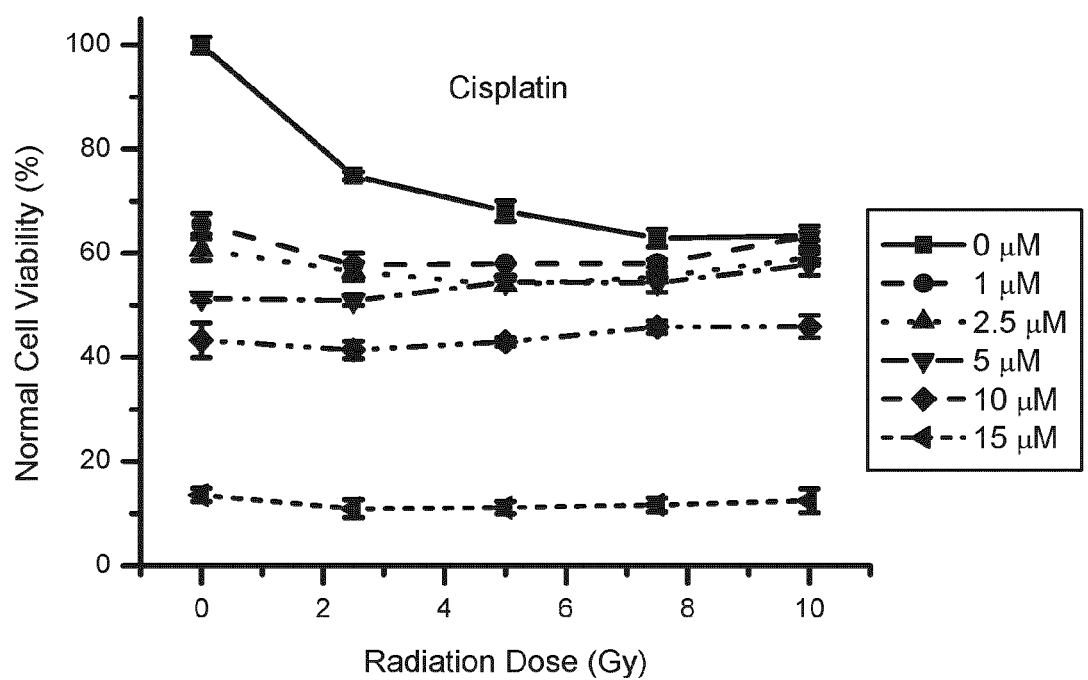

FIG. 10 illustrates cell survival rates of human normal cells (GM05757) after the 12-hr treatment of cisplatin with various concentrations, followed by 0-10 Gy 225 keV X-ray irradiation. At 12 days after irradiation, the viability of the cells in 96-well plates was measured by MTT assay. This result confirms that in spite of being highly toxic as a chemotherapeutic drug, cisplatin induced essentially no radiation toxicity. Therefore cisplatin has been used as a radiosensitizer in the clinic.

Figure 11:
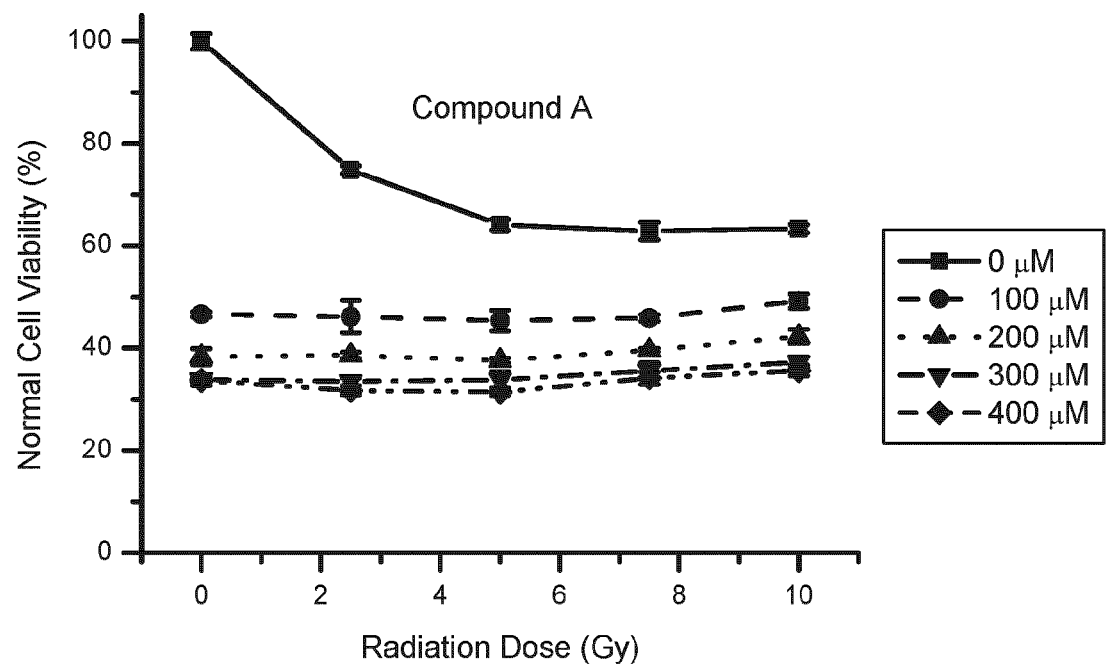

FIG. 11 illustrates cell survival rates of human normal cells (GM05757) after the 12-hr treatment of Compound A with various concentrations, followed by 0-10 Gy 225 keV X-ray irradiation. 12 days after irradiation, the viability of the cells in 96-well plates was measured by MTT assay. This result shows that the cell viability was independent of radiation doses, indicating that compound A induced no radiation toxicity.

Figure 12:
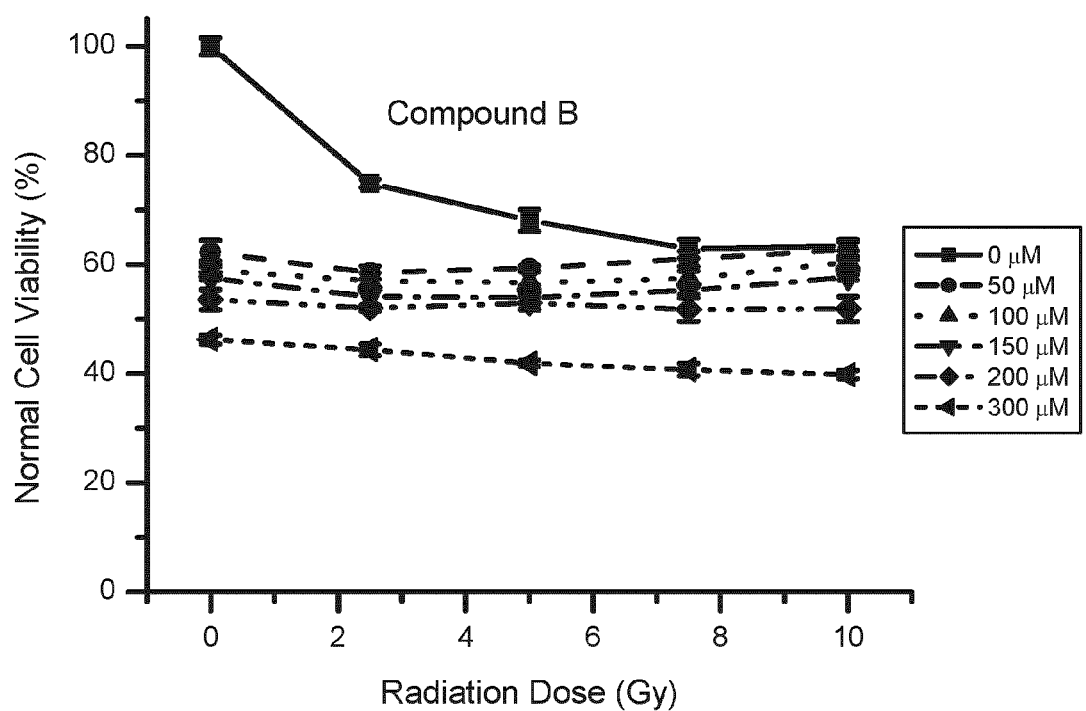

FIG. 12 illustrates cell survival rates of human normal cells (GM05757) after the 12-hr treatment of Compound B with various concentrations, followed by 0-10 Gy 225 keV X-ray irradiation. 12 days after irradiation, the viability of the cells in 96-well plates was measured by MTT assay. This result shows that the cell viability was independent of radiation doses, indicating that compound B induced no radiation toxicity.

Figure 13:
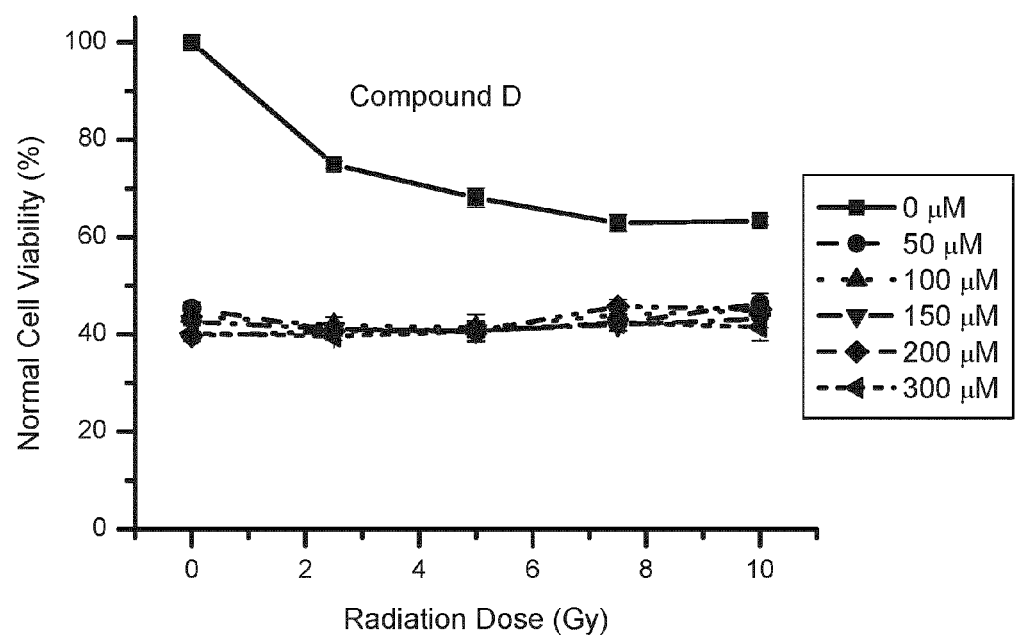

FIG. 13 illustrates cell survival rates of human normal cells (GM05757) after the 12-hr treatment of Compound D with various concentrations, followed by 0-10 Gy 225 keV X-ray irradiation. 12 days after irradiation, the viability of the cells in 96-well plates was measured by MTT assay. This result shows that the cell viability was independent of radiation doses, indicating that compound D induced no radiation toxicity.

Figure 14:
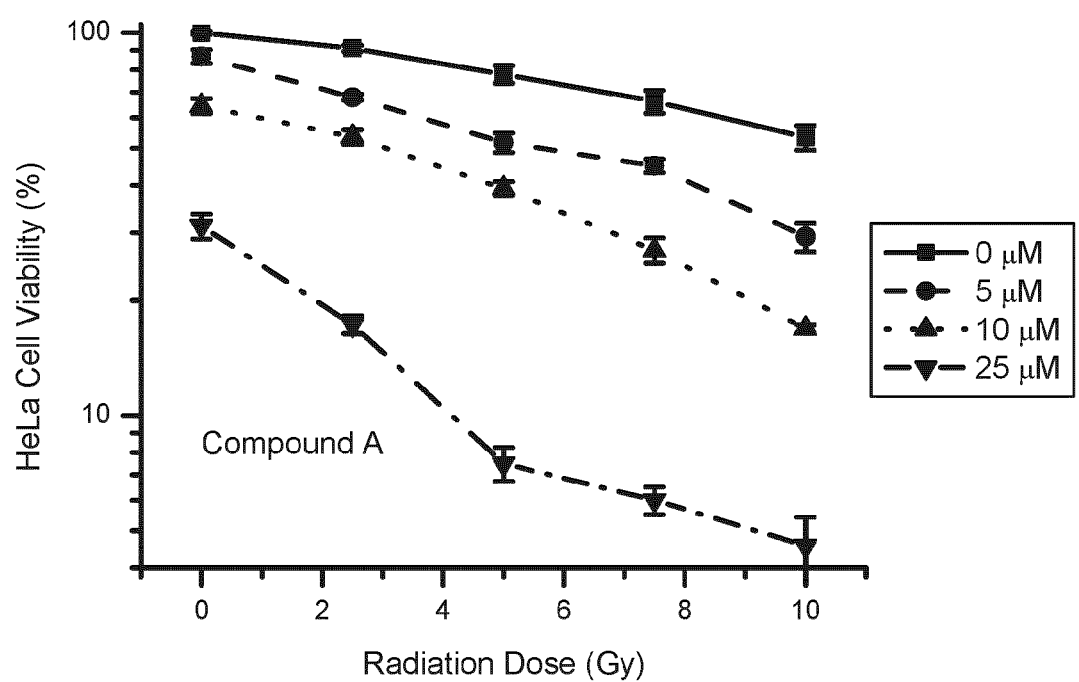

FIG. 14 illustrates cell survival rates of human cervical cancer (HeLa) cells after the 12-hr treatment of Compound A with various concentrations, followed by 0-10 Gy 225 keV X-ray irradiation. 6 days after irradiation, the viability of the cells in 96-well plates was measured by MTT assay. A significant enhancement in the radiosensitivity of cancer cells to X-ray by Compound A was observed.

Figure 15:
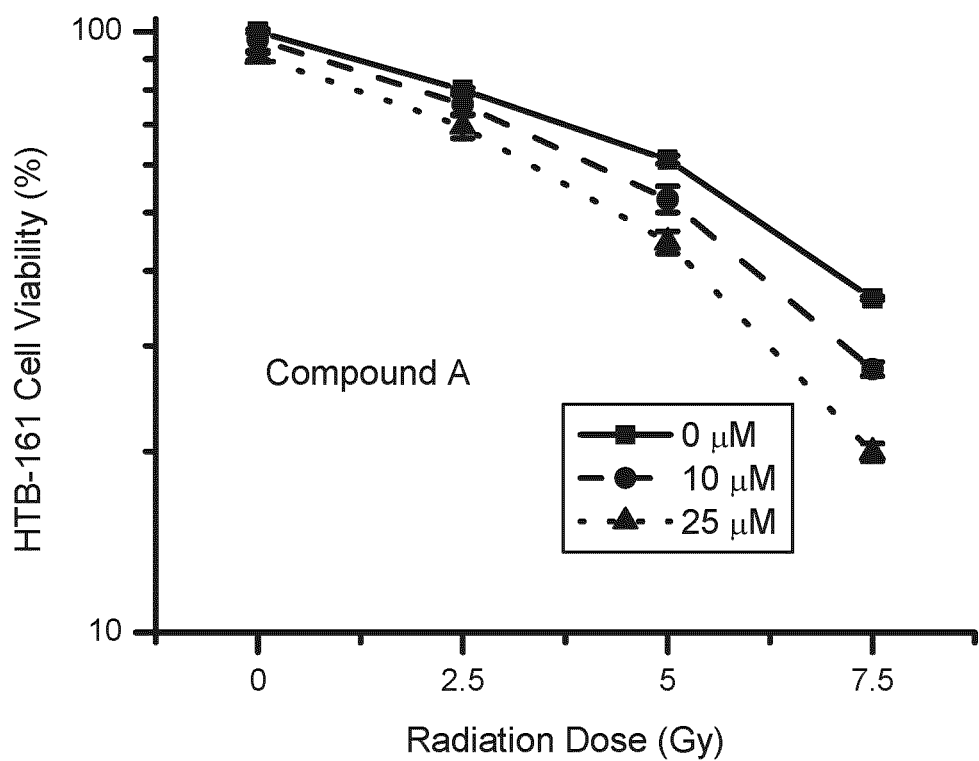

FIG. 15 illustrates cell survival rates of cisplatin-resistant human ovarian cancer (HTB-161) cells after the 12-hr treatment of Compound A with various concentrations, followed by 0-10 Gy 225 keV X-ray irradiation. 6 days after irradiation, the viability of the cells in 96-well plates was measured by MTT assay. A significant enhancement in the radiosensitivity of cisplatin-resistant cancer cells to X-ray by Compound A was observed.

Figure 16:
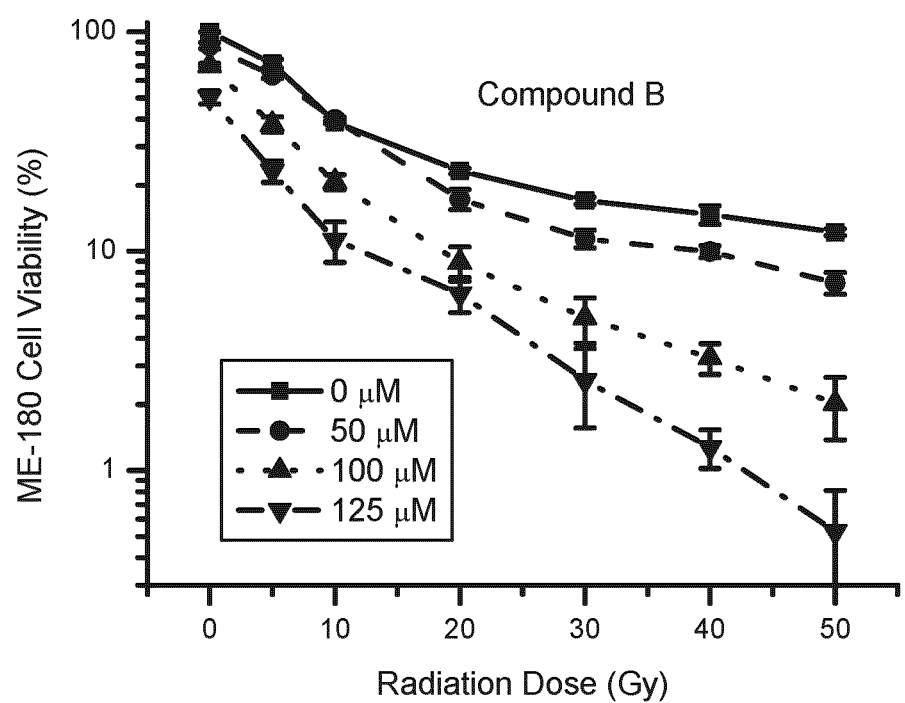

FIG. 16 illustrates cell survival rates of human cervical cancer (ME-180) cells after the 12-hr treatment of Compound B with various concentrations, followed by 0-10 Gy 225 keV X-ray irradiation. 6 days after irradiation, the viability of the cells in 96-well plates was measured by MTT assay. A significant enhancement in the radiosensitivity of cancer cells to X-ray by Compound B was observed.

Figure 17:
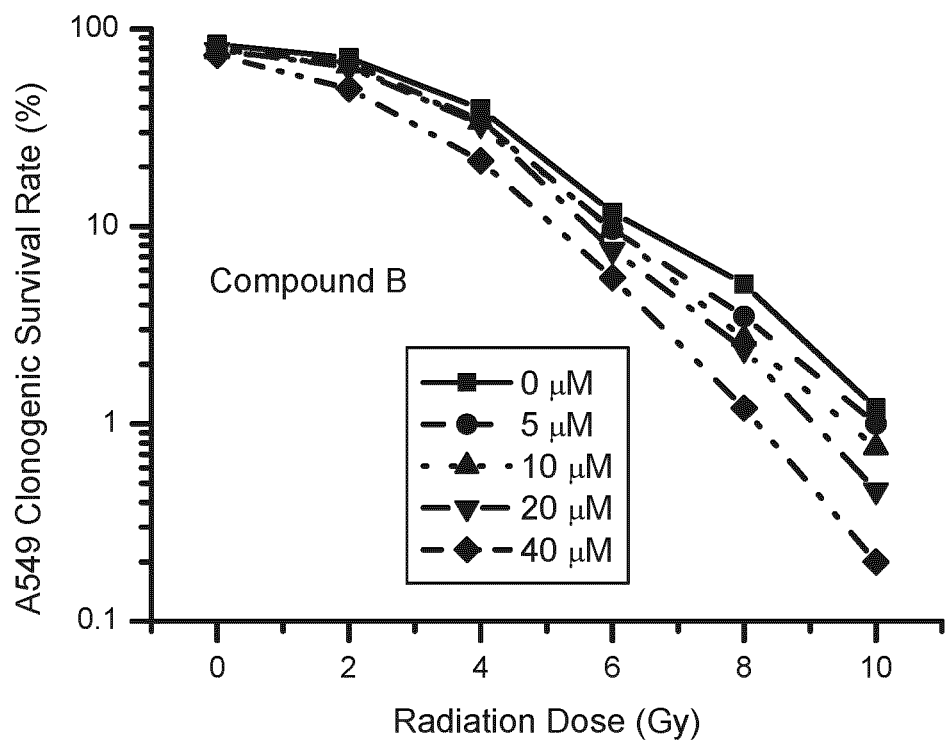

FIG. 17 illustrates cell survival rates of cisplatin-resistant human lung cancer (HTB-161) cells after the 12-hr treatment of Compound B with various concentrations, followed by 0-10 Gy 225 keV X-ray irradiation. The survival curves of the treated cells was measured by 18-day clonogenic assay. A significant enhancement in the radiosensitivity of cisplatin-resistant cancer cells to X-ray by Compound B was observed.

Figure 18:
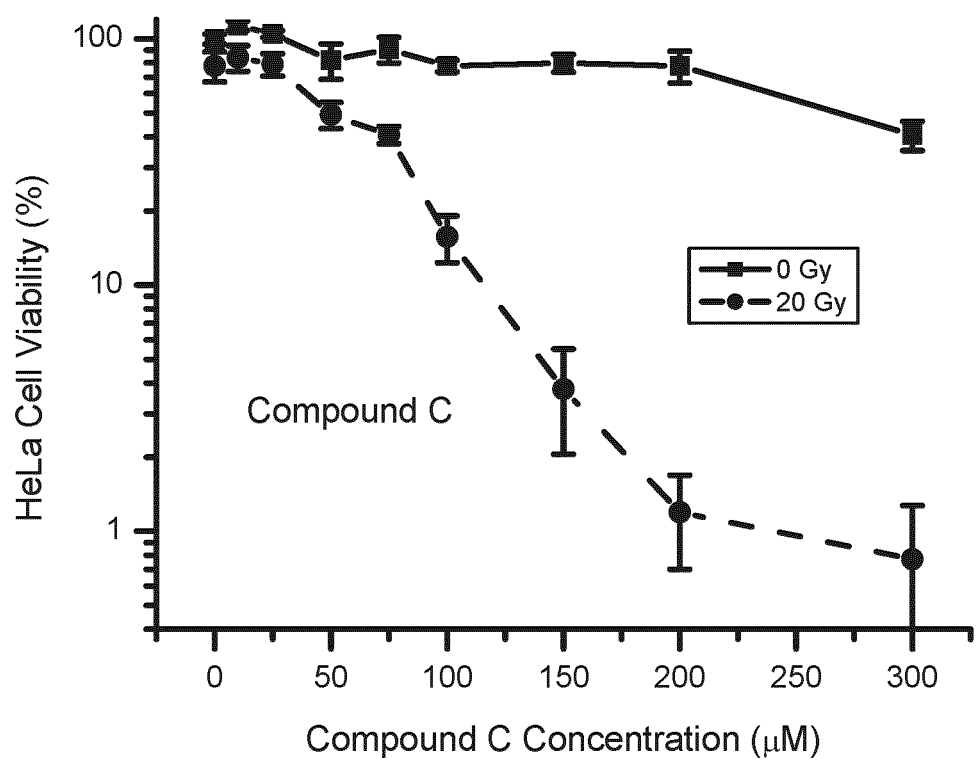

FIG. 18 illustrates cell survival rates of human cervical cancer (HeLa) cells after the 12-hr treatment of Compound C with various concentrations, followed by 0 and 20 Gy 225 keV X-ray irradiation. 6 days after irradiation, the viability of the cells in 96-well plates was measured by MTT assay. A significant enhancement in the radiosensitivity of cancer cells to X-ray by Compound C was observed.

Figure 19:
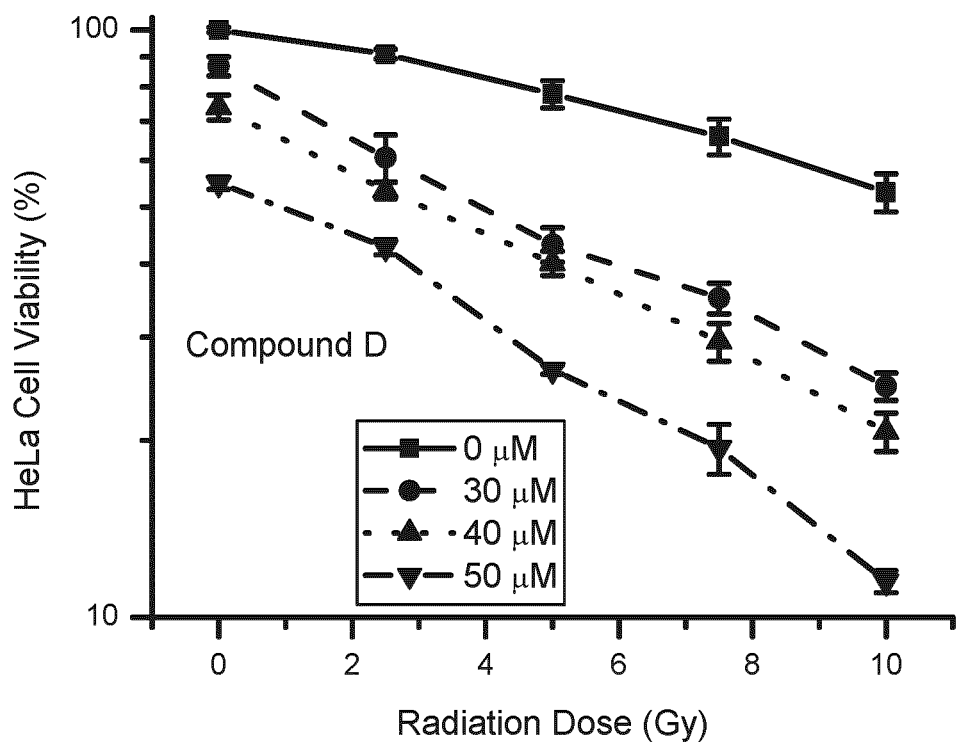

FIG. 19 illustrates cell survival rates of human cervical cancer (HeLa) cells after the 12-hr treatment of Compound D with various concentrations, followed by 0-10 Gy 225 keV X-ray irradiation. 6 days after irradiation, the viability of the cells in 96-well plates was measured by MTT assay. A significant enhancement in the radiosensitivity of cancer cells to X-ray by Compound D was observed.

Figure 20:
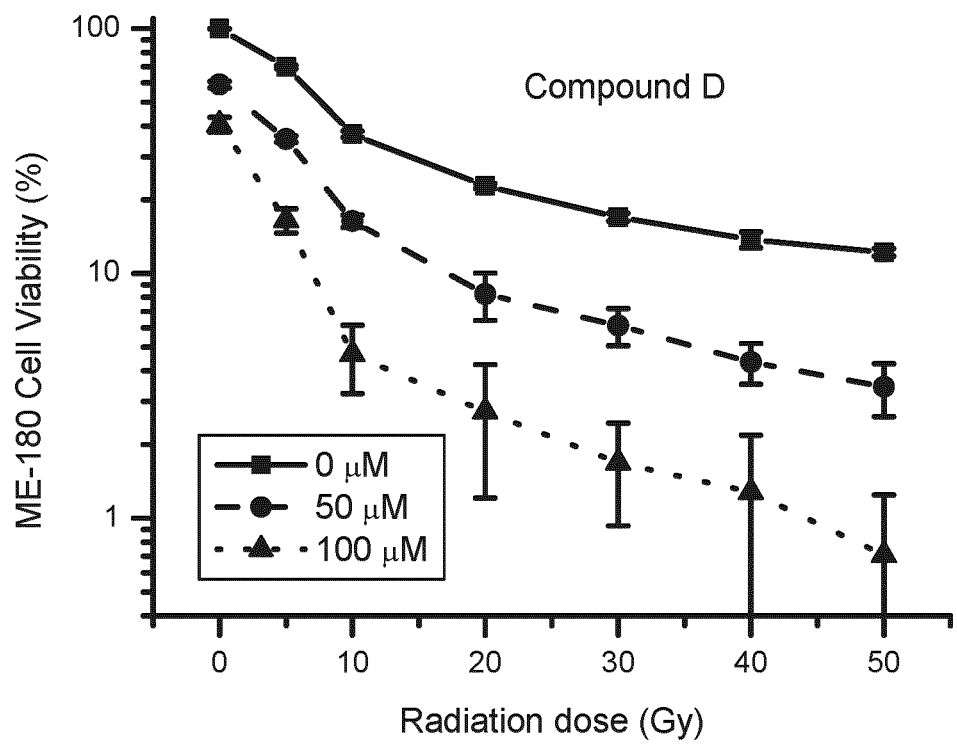

FIG. 20 illustrates cell survival rates of human cervical cancer (ME-180) cells after the 12-hr treatment of Compound D with various concentrations, followed by 0-10 Gy 225 keV X-ray irradiation. 6 days after irradiation, the viability of the cells in 96-well plates was measured by MTT assay. A significant enhancement in the radiosensitivity of cancer cells to X-ray by Compound D was observed.

Figure 21:
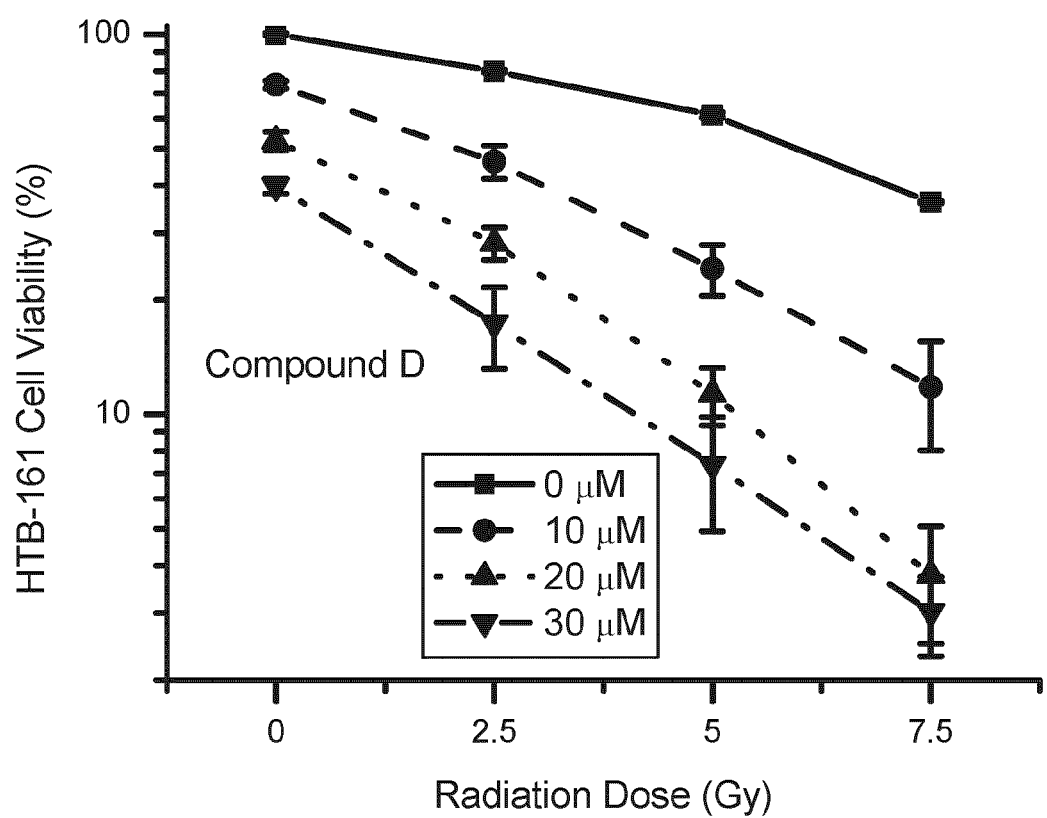

FIG. 21 illustrates cell survival rates of cisplatin-resistant human ovarian cancer (HTB-161) cells after the treatment of Compound D with various concentrations, followed by 0-7.5 Gy 225 keV X-ray irradiation. 6 days after irradiation, the viability of the cells in 96-well plates was measured by MTT assay. A significant enhancement in the radiosensitivity of cisplatin-resistant cancer cells to X-ray by Compound D was observed.

Figure 22:
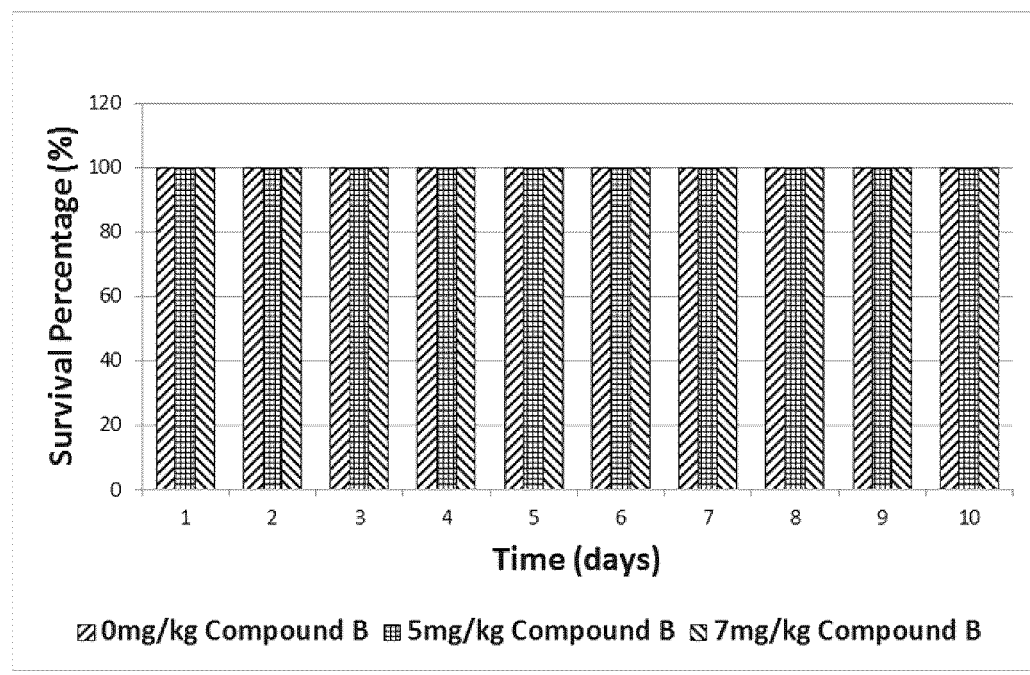

FIG. 22 shows the survival rate of mice IP injected with Compound B at various concentrations (0, 5 and 7 mg/kg) given daily for 10 days. The results show that Compound B has no overall toxicity in mice.

Figure 23:
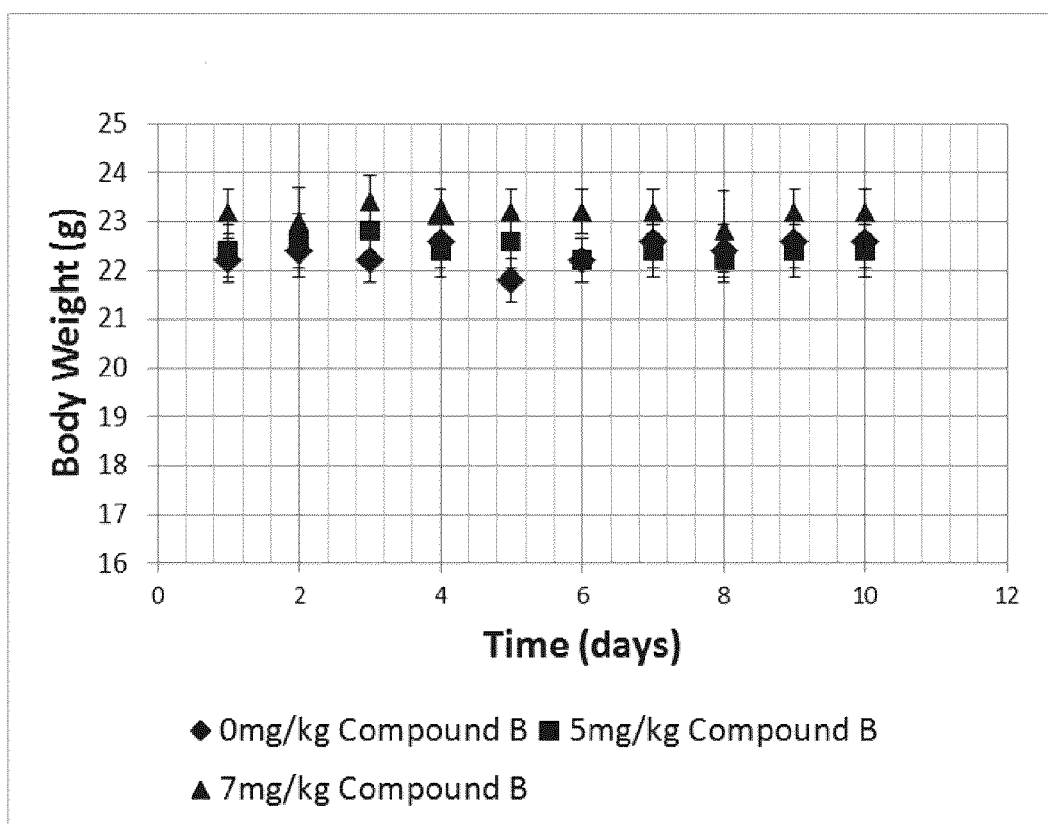

FIG. 23 shows mouse weight variation for the treatments of Compound B at various concentrations (0, 5 and 7 mg/kg) given daily for 10 days by IP injection. The results show that Compound B has no overall toxicity in mice.

Figure 24:
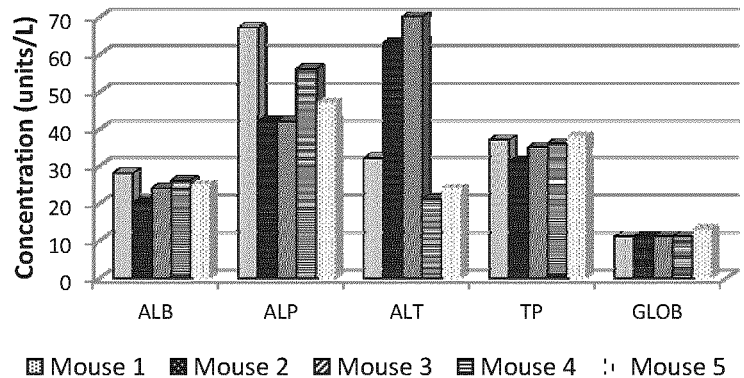
Figure 24:
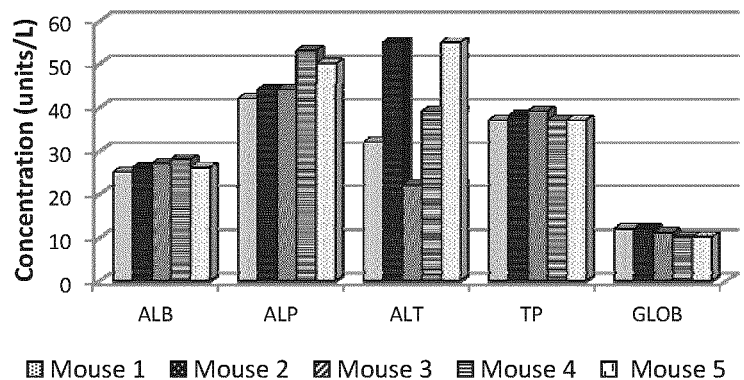
Figure 24:
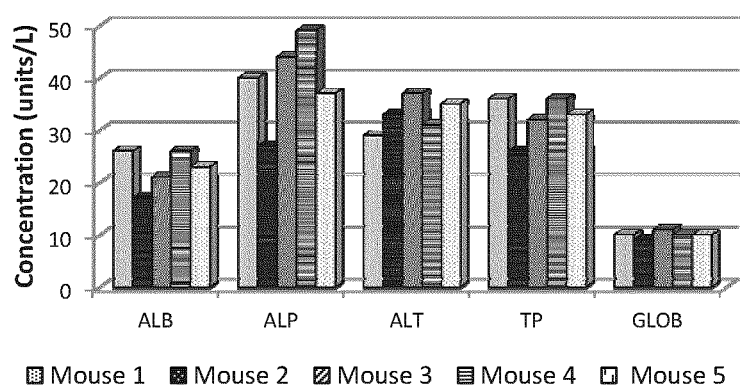

FIG. 24 shows mouse serum profile variation for the treatments of Compound B at various concentrations (0, 5 and 7 mg/kg) given daily for 10 days. The results show no acute toxicity induced by Compound B.

Figure 25:
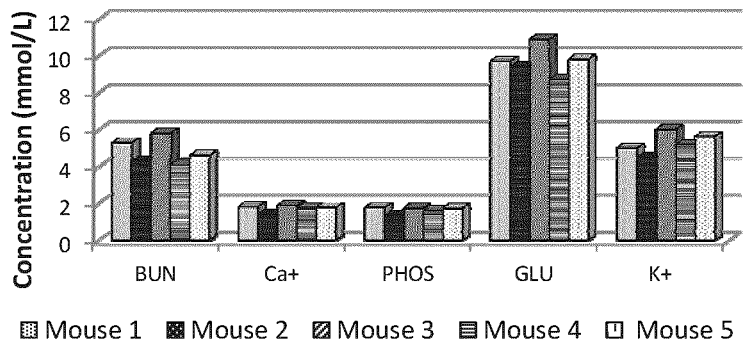
Figure 25:
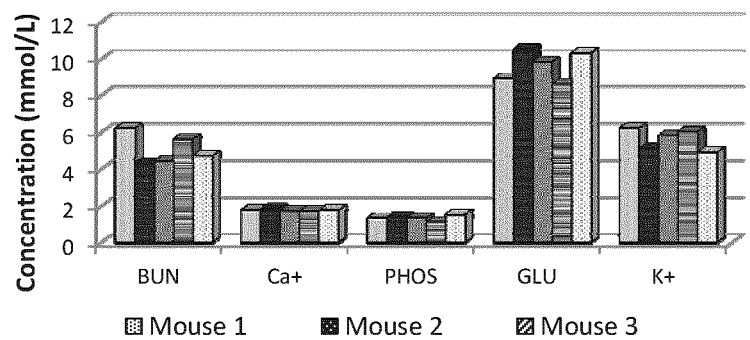
Figure 25:
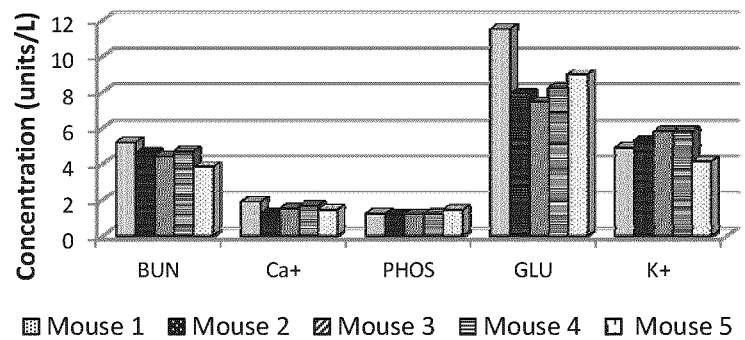

FIG. 25 shows mouse electrolyte variation for the treatments of Compound B at various concentrations (0, 5 and 7 mg/kg) given daily for 10 days. The results show no acute toxicity induced by Compound B.

Figure 26:
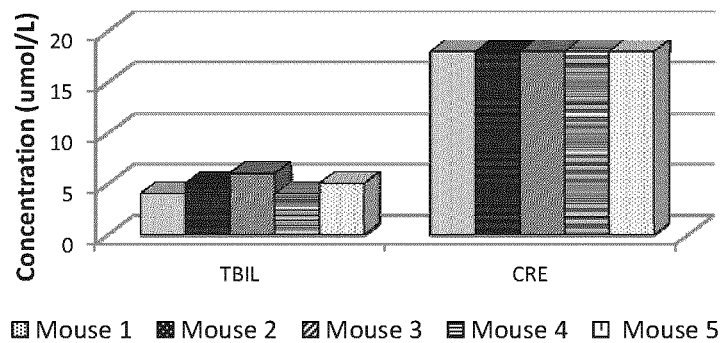
Figure 26:
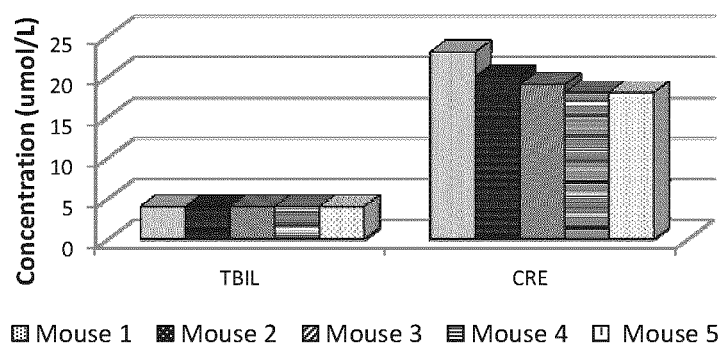
Figure 26:
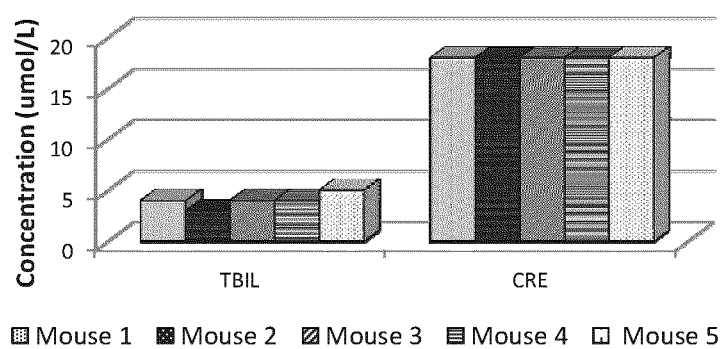

FIG. 26 shows mouse liver protein profile variation for the treatments of Compound B at various concentrations (0, 5 and 7 mg/kg) given daily for 10 days. The results show no acute toxicity induced by Compound B.

Figure 27:
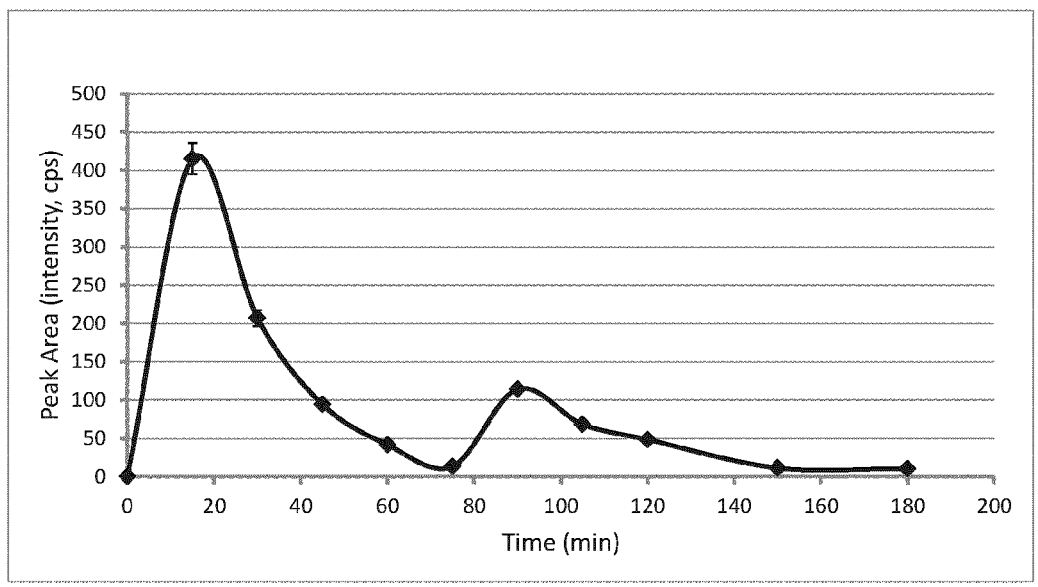

FIG. 27 shows the pharmacokinetics result that compound B was detected in the plasma. The highest concentration of compound B was observed at about 20 minutes after the i.p. injection and dropped to nearly zero at about 3 hr after injection.

Figure 28:
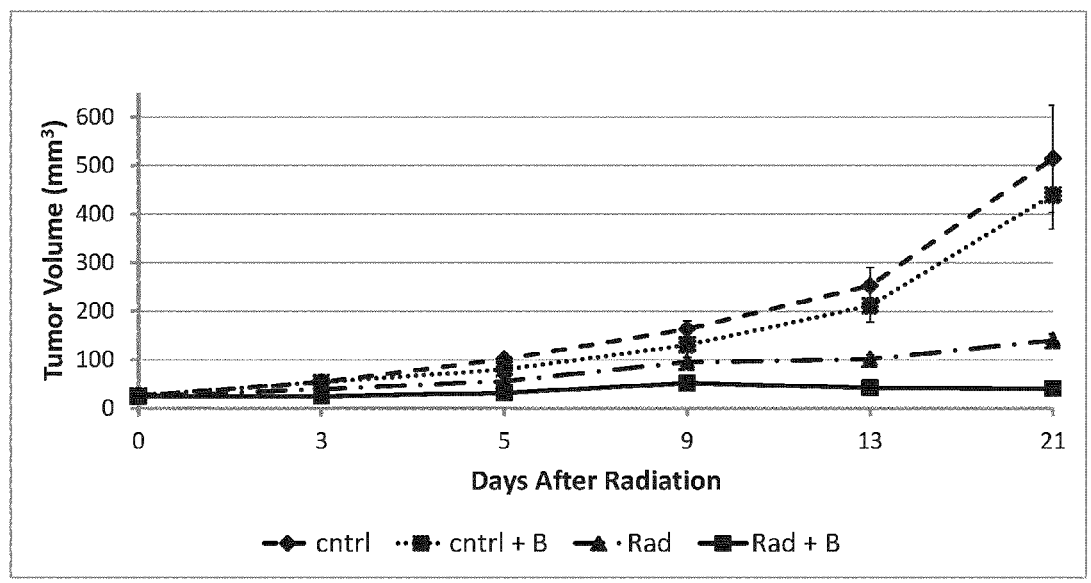

FIG. 28 shows tumor volume growth curves for the treatments of control, 7 mg/kg Compound B only, 15 Gy 225 keV x-ray only, 7 mg/mg Compound B plus 15 Gy 225 keV x-ray. Compound B was given by IP injection at 1 hr prior to x-ray irradiation.

Figure 29:
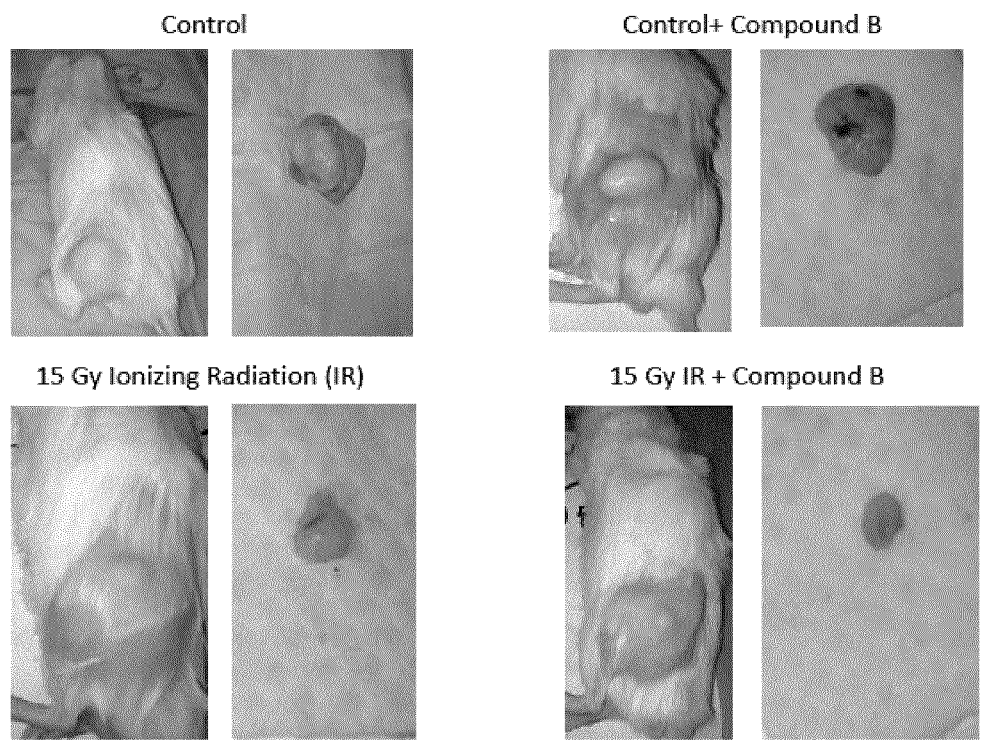

FIG. 29 shows photos of tumor growths in mice at 19 days after treatments of 7 mg/kg Compound B and/or 15 Gy x-rays ionizing radiation (IR), compared to the control.

Figure 30:
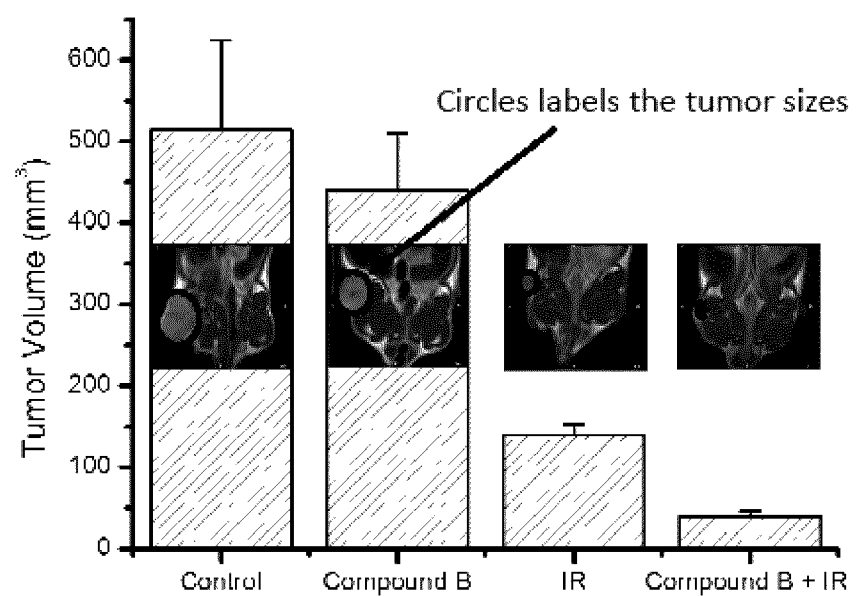

FIG. 30 shows tumor volumes and MRI images of mice at Day 21 after treatments of 7 mg/kg Compound B and/or 15 Gy x-rays ionizing radiation (IR), compared to the control. The combination of Compound B with IR resulted in a most significant shrinkage of the tumor in mice.

DETAILED DESCRIPTION

Generally, the present disclosure relates to radiosensitizer compounds useful in combination with ionizing radiation, e.g. to enhance radiation therapy. The compounds have been demonstrated to enhance the effects of radiation therapy in a synergistic manner. Accordingly, the present disclosure also relates to a combination therapy for treating cancer and other disorders treatable by radiation therapy. Also disclosed herein are compounds, compositions, methods, uses, commercial packages and kits relating to the radiosensitizing compounds. While the compounds disclosed herein are effective radiosensitizers, they were found to be significantly less toxic to normal cells than the platinum-containing radiosensitizer, cisplatin, even at doses up to 200 µM.

Radiosensitizer Compounds (RSCs)

As used herein, a "radiosenzitizer compound" refers to a non-platinum-containing compound as defined herein that may be used to enhance radiotherapy, for example, in the treatment of cancer and other disorders treatable by ionizing radiation. The terms "compound", "molecule" and "agent" may be used interchangeably herein.

The radiosensitizer compounds of the present disclosure interact with ionization radiation to enhance the effect of said ionizing radiation thereby providing a synergistic combination. Without being bound by theory, the radiosensitizer compounds are believed to be highly reactive with prehydrated electrons ($e_{pre}^-$) generated by radiolysis of water in the cells exposed to ionizing radiation. Some general features of the radiosensitizing compounds of the present disclosure are that they comprise an aromatic ring (rather than a platinum coordinating ion), coupled to one or more electron transfer promoters, such as $NH_2$ groups, and one or more electron-accepting leaving groups, such as halogen.

It has been demonstrated that the radiosensitizer compounds disclosed herein are non-toxic toward normal cells, even at very high doses up to 200 µM, while their combination with ionizing radiation can effectively kill the cancer cells in vitro or in vivo. The compounds are believed to have a low affinity to normal cells, possibly due to the lack of a reductive intracellular environment, and to have no or low systematic and acute toxicity in the body. They are highly effective radiosensitizing agents that can enhance the preferential killing of cancer cells by ionizing radiation and are therefore believed to be useful for enhancing radiotherapy of cancer and potentially other disorders treatable by radiation. The disclosed compounds are expected to be superior to cisplatin, which is highly toxic, and halopyrimidines, which are relatively ineffective as radiosensitizers.

In some embodiments, the biocompatible radiosensitizer compound for use in combination with ionizing radiation has the general formula I:

(I)

wherein A is a 5- or 6-membered aryl or heteroaryl ring containing 0-2 ring heteroatoms selected from the group consisting of N, O and S, the remaining ring atoms being carbon, $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of $R^a$ and $R^b$ is an electron transfer promoter; $R^c$ is, independently for each occurrence, H, OH, alkyl, alkoxy, alkenyl, alkynyl, cycloalkyl, cycloalkenyl, cycloalkynyl, aryl, heterocyclyl, heteroaryl, a leaving group, or two adjacent $R^c$ groups taken together with the ring atoms to which they are attached form a 5- or 6-membered saturated, partially saturated or unsaturated ring which contains 0-2 ring heteroatoms selected from N, O and S and which can be optionally substituted with 1-4 $R^d$; wherein at least one $R^c$ is a leaving group; $R^d$ is independently OH, alkyl, alkoxy, alkenyl, alkynyl, cycloalkyl, cycloalkenyl, cycloalkynyl, aryl, heterocyclyl or heteroaryl; and n=1-4, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In some embodiments, the radiosensitizer compound has the general formula II:

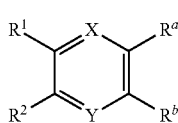

(II)

wherein: X and Y are independently C—$R^3$ or N; $R^3$ is H, OH, halogen, alkyl, alkoxy, alkenyl, alkynyl, cycloalkyl, cycloalkenyl, cycloalkynyl, aryl, heterocyclyl, or heteroaryl; $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of $R^a$ and $R^b$ is an electron transfer promoter; $R^1$ and $R^2$ are, independently, H, OH, alkyl, alkoxy, alkenyl, alkynyl, cycloalkyl, cycloalkenyl, cycloalkynyl, aryl, heterocyclyl, heteroaryl, or a leaving group; wherein at least one of $R^1$ and $R^2$ is a leaving group, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

In some embodiments, the radiosensitizer compound has the general formula III,

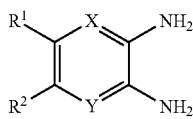

(III)

wherein X and Y are independently C—$R^3$ or N; $R^3$ is H, OH, halogen, alkyl, alkoxy, alkenyl, alkynyl, cycloalkyl, cycloalkenyl, cycloalkynyl, aryl, heterocyclyl, or heteroaryl; $R^1$ and $R^2$ are, independently, H, OH, alkyl, alkoxy, alkenyl, alkynyl, cycloalkyl, cycloalkenyl, cycloalkynyl, aryl, heterocyclyl, heteroaryl, or a leaving group; wherein at least one of $R^1$ and $R^2$ is a leaving group, wherein each of the alkyl, alkoxy, alkenyl, alkynyl, cycloalkyl, cycloalkenyl, cycloalkynyl, aryl, heterocyclyl and heteroaryl moieties is optionally substituted; or a pharmaceutically acceptable salt thereof.

Aromatic Ring Systems

In each of the general formulas I, II and III, the core of the molecule is a conjugated or aromatic ring system that may consist of one aryl or heteroaryl ring (monocyclic), or may consist of a multiple rings (polycyclic). In some cases, the aromatic core may comprise 2 or 3 fused rings to form a bi-cyclic, or tri-cyclic core, respectively. Aromatic ring systems are capable of transporting an electron transiently stabilized by the electron transfer promoter, such as $NH_2$ groups, acquired through reaction with a prehydrated electron, to the site of a leaving group. When a temporary anion of the molecule is formed, it can rapidly cause a loss of the leaving group, such as a stable anion, and produce a highly reactive neutral radical.

The aromatic core may be single 5- or 6-membered aromatic ring, such as aryl or heteroaryl. Some examples of 6-membered mono-cyclic rings include, but are not limited to, benzene, pyridine, and pyrazine. Some examples of 5-membered heteroaryl rings include, but are not limited to, furan, pyrole, thiophene and oxazole.

In some embodiments, e.g. embodiments of general Formula I, II or III, the compound comprises a 5- or 6-membered aryl or heteroaryl ring containing 0-2 ring heteroatoms selected from the group consisting of N, O and S, the remaining ring atoms being carbon. In some cases, the core is a 6-membered aromatic ring containing 0, 1 or 2 ring heteroatoms selected from N, such as benzene (0 N), pyridine (1 N), or pyrazine (2 N). In some cases, the core is a 6-membered aryl ring containing 0 ring heteroatoms, such as benzene. In some cases, the core is a 6-membered heteroaryl ring containing 1 or 2 ring heteroatoms selected from N, such as pyridine (1 N) or pyrazine (2 N).

In some embodiments, substituents (e.g. $R^c$ in Formula I) adjacent one another on the core ring may, together with the ring atoms to which they are attached, form a 5- or 6-membered saturated, partially saturated or unsaturated ring, thereby forming a polycyclic ring system. Some examples of fused bi-cyclic 6-membered rings include, but are not limited to, naphthalene, quinolone, isoquinoline, quinoxaline, quinazoline, cinnoline and phthalazine. Some examples of fused tri-cyclic 6-membered rings include, but are not limited to, anthracene, phenanthracene, and acridine. In some cases, a polycyclic ring system may comprise a combination of 5- and 6-membered ring moieties. Where the core is a polycyclic ring system, it is desirable that the compound as a whole retain its ability to transiently stabilize and transport an electron to the site of a leaving group such that a reactive radical can be formed.

Electron Transfer Promoters

The radiosensitizer compounds of the present disclosure comprise one or more electron transfer promoters coupled to the aromatic ring system (e.g. one or both of $R^a$ and $R^b$ in Formula I or II, and —$NH_2$ in Formula III). A "electron transfer promoter", as used herein, is an atom or functional group that assists in capturing and transiently stabilizing a prehydrated electron. The electron is then transported through the aromatic ring system to cause breakage of a bond between a ring carbon atom and a leaving group. Once the leaving group breaks away from the ring, the resulting neutral radical is highly reactive, e.g. with DNA to cause DNA damage and death of a cancer cell. Thus, it is believed that the electron transfer promoter, preferably two electron transfer promoters in close proximity to one another, activates the radiosensitizer molecule, making it more reactive with a prehydrated electron generated during radiolysis.

Where there are multiple electron transfer promoters on the molecule (e.g. $R^a$ and $R^b$ are both electron transfer promoters), the electron transfer promoters may be the same or different. In some embodiments, the electron transfer promoters are the same. In preferred embodiments, two electron transfer promoters are positioned in close proximity to one another on the ring, e.g. on adjacent ring carbons. This is a particularly effective arrangement for capturing and transferring electrons, particularly when strong leaving groups are present on the ring.

Examples of electron transfer promoters include but are not limited to —$NH_2$, —NHR, —$NR_2$, —OH, —OR, —O—, —$NHCOCH_3$, —NHCOR, —$OCH_3$, —OR, —$CH_3$, —$C_2H_5$, R, and —$C_6H_5$.

In some embodiments, e.g. of Formula I, II or III, the electron transfer promoter is selected from the group consisting of —$NH_2$, —NHR, —$NR_2$, —OH, —OR, —O—, —$NHCOCH_3$, —NHCOR, —$OCH_3$, —OR, —$CH_3$, —$C_2H_5$, R, and —$C_6H_5$. In some embodiments, e.g. of Formula I, II or II, the electron transfer promoter is selected from the group consisting of —$NH_2$, —NHR, —$NR_2$, —OH, —$NHCOCH_3$, —NHCOR, —$OCH_3$, and —OR. In some embodiments, e.g. of Formula I, II or II, the electron transfer promoter is a selected form the group consisting of —$NH_2$, —NHR, —$NR_2$, —OH, and —O—. In some embodiments, the electron transfer promoter is selected from the group consisting of —$NH_2$, —NHR, —$NR_2$, and —OH. In some embodiments, the electron transfer promoter is selected form the group consisting of —$NH_2$, —NHR, —$NR_2$. In some embodiments, the electron transfer promoter is —$NH_2$. In some embodiments, the electron transfer promoter is —NHR. In some embodiments, the electron transfer promoter is —$NR_2$. In some embodiments, e.g. of Formula I, II or II, the electron transfer promoter is selected from the group consisting of —$NHCOCH_3$, —NHCOR, —$OCH_3$, and —OR.

R in any of the above may, for example, be substituted or unsubstituted alkyl, alkoxy, alkenyl, alkynyl, cycloalkyl, cycloalkenyl, cycloalkynyl, aryl, heterocyclyl or heteroaryl groups. In the case of $R_2$, each R may be the same or different. In some embodiments, R is substituted or unsubstituted alkyl.

In some embodiments, e.g. of Formula I or II, one of $R^a$ and $R^b$ is an electron transfer promoter. In some embodiments, both of $R^a$ and $R^b$ is an electron transfer promoter. In some embodiments, both of $R^a$ and $R^b$ are the same electron transfer promoter. In some embodiments, $R^a$ and $R^b$ are positioned on adjacent ring atoms. In some embodiments, a leaving group is positioned meta, ortho or para to the electron transfer promoter. In some embodiments, a leaving group is positioned meta to the electron transfer promoter. In some embodiments, a leaving group is positioned ortho to the electron transfer promoter. In some embodiments, a leaving group is positioned para to the electron transfer promoter.

Leaving Groups

The radiosensitizer compounds of the present disclosure comprise one or more leaving groups coupled to the aromatic ring system (e.g. one or both of $R^1$ and $R^2$ in Formula I, II or III). Additional leaving groups may also be provided as substituents on the aromatic ring. Where there are multiple leaving groups, the leaving groups may be the same or different. In some embodiments, the leaving groups are the same. The presence of a strong leaving group on the molecule can enhance the reactivity of the molecule with prehydrated electrons generated during radiolysis, particularly when the leaving group is operatively positioned with respect to the electron transfer promoter (e.g. within 1, 2 or 3 ring atoms).

A leaving group, as used herein, is a molecular fragment that departs with a pair of electrons in heterolytic bond cleavage. Leaving groups can be anions or neutral molecules, but in either case it is crucial that the leaving group be able to stabilize the additional electron density that results from bond heterolysis. Common anionic leaving groups include, but are not limited to, halides, such as, Cl, Br, and I (e.g. $Cl^-$, $Br^-$, $I^-$), and sulfonate esters, such as tosylate, nosylate, mesylate and triflate. Other leaving groups include, but are not limited to, dinitrogen, dialkyl ethers, alcohols, nitrates, phosphates, and other inorganic esters. In accordance with the present disclosure, the leaving group must be a biocompatible leaving group.

In some embodiments, e.g. of Formula I, II or II, the leaving group is an anionic leaving group. In some embodiments, the leaving group is halogen. In some embodiments, the leaving group is Cl, Br or I. In some embodiments, the leaving group is Cl. In some embodiments, the leaving group is Br. In some embodiments, the leaving group is I.

In some embodiments of Formula I, two $R^c$ groups on Ring A are leaving groups. In some embodiments, the leaving groups are halogen selected from the group consisting of Cl, Br and I.

In some embodiments of Formula I, Ring A is a 6-membered aryl or heteroaryl ring, such as benzene, pyridine or pyrazine, each of $R^a$ and $R^b$ are $NH_2$; two $R^c$ substituents on Ring A are halogen each positioned meta to one of $R^a$ and $R^b$ on Ring A; and any remaining $R^c$ groups are as defined herein. In some embodiments, Ring A is benzene. In some embodiments, where Ring A is benzene, the remaining carbons on Ring A are unsubstituted carbon. In some embodiments, Ring A is pyridine. In some embodiments, where Ring A is pyridine, the remaining carbon on Ring A is unsubstituted. In some embodiments, Ring A is pyrazine.

In some embodiments, the leaving group is positioned ortho (e.g. within 1 ring atom), meta (e.g. within 2 ring atoms) or para (e.g. within 3 ring atoms) to the electron transfer promoter.

Substituents

In embodiments of Formula I, II or III, carbon atoms may be unsubstituted or substituted, unless otherwise specified.

In embodiments, of Formula I, II or III, unless defined otherwise, ring carbon atoms may be unsubstituted or substituted. Substituents may include, for example, OH, halogen, alkyl, alkoxy, alkenyl, alkynyl, cycloalkyl, cycloalkenyl, cycloalkynyl, aryl, heterocyclyl or heteroaryl groups. Each of the carbon-based substituents (e.g. alkyl, alkoxy, alkenyl, alkynyl, cycloalkyl, cycloalkenyl, cycloalkynyl, aryl, heterocyclyl or heteroaryl) may optionally be further substituted.

In embodiments of Formula I, $R^c$ is, independently for each occurrence, H, OH, alkyl, alkoxy, alkenyl, alkynyl, cycloalkyl, cycloalkenyl, cycloalkynyl, aryl, heterocyclyl, heteroaryl, a leaving group, or two adjacent $R^c$ groups taken together with the ring atoms to which they are attached form a 5- or 6-membered saturated, partially saturated or unsaturated ring which contains 0-2 ring heteroatoms selected from N, O and S and which can be optionally substituted with 1-4 $R^d$; wherein at least one $R^c$ is a leaving group. $R^d$ is independently OH, alkyl, alkoxy, alkenyl, alkynyl, cycloalkyl, cycloalkenyl, cycloalkynyl, aryl, heterocyclyl or heteroaryl; and n=1-4 (e.g. 1, 2, 3 or 4). Each of the alkyl, alkoxy, alkenyl, alkynyl, cycloalkyl, cycloalkenyl, cycloalkynyl, aryl, heterocyclyl and heteroaryl moieties may be optionally substituted.

In embodiments of Formula I and II, $R^a$ and $R^b$ are, independently, H, OH, alkyl, alkoxy, alkenyl, alkynyl, cycloalkyl, cycloalkenyl, cycloalkynyl, aryl, heterocyclyl, heteroaryl or an electron transfer promoter, wherein at least one of Ra and Rb is an electron transfer promoter. Each of the alkyl, alkoxy, alkenyl, alkynyl, cycloalkyl, cycloalkenyl, cycloalkynyl, aryl, heterocyclyl and heteroaryl moieties may be optionally substituted.

In embodiments of formula II or III, where X and Y are independently C—$R^3$ or N, $R^3$ may H, OH, halogen, alkyl, alkoxy, alkenyl, alkynyl, cycloalkyl, cycloalkenyl, cycloalkynyl, aryl, heterocyclyl, or heteroaryl. Each of the alkyl, alkoxy, alkenyl, alkynyl, cycloalkyl, cycloalkenyl, cycloalkynyl, aryl, heterocyclyl and heteroaryl moieties may be optionally substituted.

In embodiments of formula II or III, $R^1$ and $R^2$ are, independently, H, OH, alkyl, alkoxy, alkenyl, alkynyl, cycloalkyl, cycloalkenyl, cycloalkynyl, aryl, heterocyclyl, heteroaryl, or a leaving group. Each of the alkyl, alkoxy, alkenyl, alkynyl, cycloalkyl, cycloalkenyl, cycloalkynyl, aryl, heterocyclyl and heteroaryl moieties may be optionally substituted. In the above, at least one of $R^1$ and $R^2$ is a leaving group. In some embodiments, both $R^1$ and $R^2$ are leaving groups, where $R^1$ and $R^2$ may be the same or different.

Unless otherwise specified, optionally substituted carbon-based groups above may further include one or more functional groups on the substituent, such as hydroxyl, amino, amido, cyano, nitro, carboxyl, ester, ether, ketone, aldehyde, aryl, and heteroaryl, or a combination thereof.

A skilled person will be able to modify the compounds disclosed herein to produce numerous radiosensitizing compounds in accordance with the present disclosure. When selecting substituents, factors such as stability, solubility, toxicity and reactivity (e.g. reactivity with a prehydrated electron) of the resulting compound, among other factors, should be considered.

Non-Limiting Exemplary Radiosensitizer Compounds

Some exemplary non-limiting radiosensitizing compounds of the present disclosure are shown below:

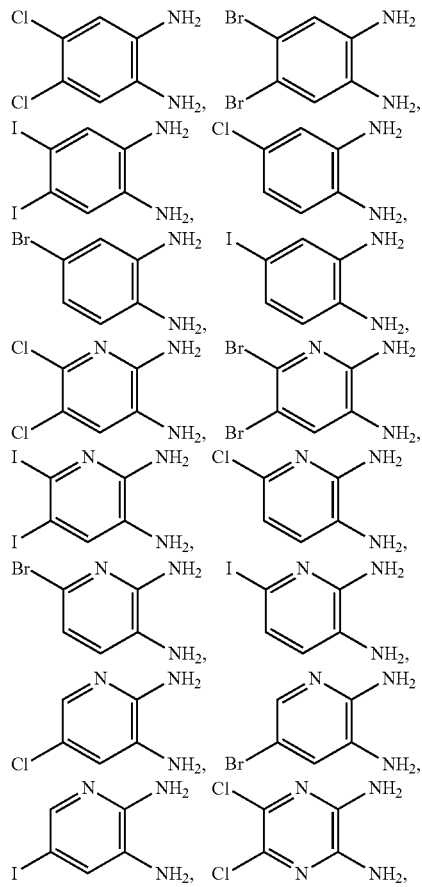

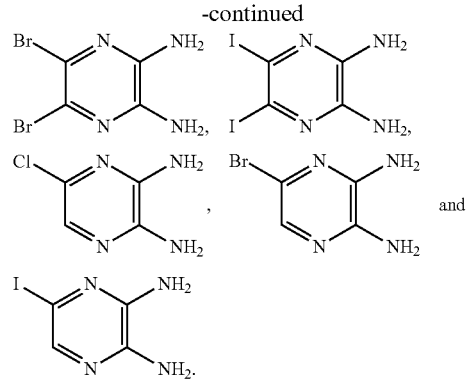

In each of the above exemplary embodiments, the radiosensitizer compound has a comprises a 6-membered aryl or heteroaryl ring selected from benzene, pyridine and pyrazine; two $NH_2$ electron transfer promoter groups positioned adjacent to one another on the ring, and at least one halogen leaving group positioned meta to one of the $NH^2$ groups. In some embodiments, a halogen leaving group is positioned meta to each of the $NH_2$ groups. It has been found that compounds having this structure are highly effective. Without being bound by theory, it is believed that such embodiments are particularly effective due to combination of two strong electron transfer promoters in close proximity to one another on the aromatic ring system, capable of capturing a prehydrated electron and transporting it through the ring to the site of a nearby leaving group to thereby form a highly-reactive radial that can attack DNA and cause cancer cell death.

In some embodiments, the radiosensitizer compound is selected from the group consisting of:

In some embodiments, the radiosensitizer compound is selected from the group consisting of:

In some embodiments, the radiosensitizer compound is selected from the group consisting of:

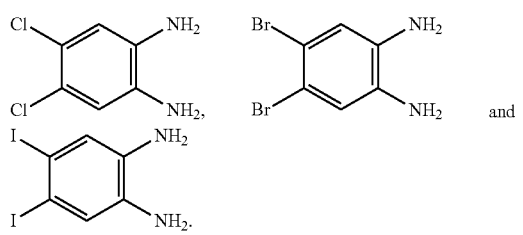

Electron Affinity

The electron affinity ($E_A$) of an atom or molecule is generally defined as the energy change when an electron is added to a neutral atom or molecule to form a negative ion:

$$X + e^- \rightarrow X^- + \text{energy}.$$

Molecules having a positive electron affinity (e.g. >0 eV) are more susceptible to receiving electrons than molecules having a negative electron affinity (e.g. <0.0 eV). In accordance with the present disclosure, a positive electron affinity is a desirable property as it relates to the reactivity of the radiosensitizer molecules with prehydrated electrons ($e_{pre}^-$) generated during radiolysis. It is therefore preferable that the radiosensitizer molecules have an electron affinity greater than 0.0 eV.

In some embodiments, e.g. embodiments of Formula I, II or III, the electron affinity of the radiosensitizer compounds (RSCs) disclosed herein is positive (e.g. >0.0 eV). In some embodiments, the electron affinity the RSC is between about 0.0 eV and about +5.0 eV, between about 0.0 eV and about +4.0 eV, between about 0.0 eV and about +3.0 eV, or between about 0.0 eV and about +2.5 eV.

In some embodiments, the electron affinity the RSC is between about +0.2 eV and about +5.0 eV, or between about +0.2 eV and about +4.0 eV, or between about +0.2 eV and about +3.0, or between about +0.2 eV and about +2.0 eV.

In some embodiments, the electron affinity the RSC is between about +0.5 eV and about +3.0 eV, between about +0.5 eV and about +2.5 eV, between about +0.5 eV and about +2.0 eV, or between about +0.5 eV and about +1.5 eV.

The electron affinity of a molecule may be determined by skilled persons using methods known in the art.

Radiolabelled Compounds

The radiosensitizer compounds of the present disclosure may be radiolabelled, i.e., said compounds may contain one or more atoms containing an atomic mass or mass number different from the atomic mass or mass number ordinarily found in nature. Exemplary radioisotopes of hydrogen, carbon, phosphorous, fluorine and chlorine include 3H, 14C, 32P, 35S, 43F and 36Cl, respectively. Radiolabelled compounds can generally be prepared by methods well known to those skilled in the art. In some cases, such radiolabelled compounds can be prepared by carrying out general synthetic procedures and substituting a readily available radiolabelled reagent for a non-radiolabelled reagent.

Chemical Definitions

The following well-known chemical terms have the following general meanings, unless otherwise specified.

As used herein, the term "aryl" means a substituted or unsubstituted aromatic hydrocarbon ring system having 6-14 ring atoms, e.g. 6 ring atoms, which may be a mono-, bi- or tri-cyclic aromatic ring system, including but not limited to those aryl groups in the molecules disclosed or exemplified herein. In some embodiments disclosed herein, "aryl" denotes a 6-membered aromatic ring, which may optionally be fused to one or more aromatic or non-aromatic rings.

The term "alkyl" denotes a saturated linear or branched hydrocarbon group containing, e.g., from 1 to 10 carbon atoms, e.g. from 1 to 6 carbon atoms or from 1 to 4 carbon atoms, for example, methyl, ethyl, propyl, isopropyl, n-butyl, i-butyl, 2-butyl, t-butyl including but not limited to those alkyl groups in the molecules disclosed or exemplified herein. The term "lower alkyl" may also be used and it typically refers to a linear or branched hydrocarbon group containing 1-6 carbon atoms (e.g. $C_1$-$C_6$ alkyl). $C_1$-$C_6$ alkyl is intended to include $C_1$, $C_2$, $C_3$, $C_4$, $C_5$, and $C_6$ alkyl groups. Furthermore, alkyl groups may be substituted or unsubstituted.

The term "alkoxy" denotes a group wherein the alkyl residues are as defined above, and which is attached via an oxygen atom, e.g. methoxy and ethoxy. Alkoxy can optionally be substituted with one or more substituents. For example, "alkoxy" refers to groups —O-alkyl, wherein the alkyl group is as defined above. Examples of "alkoxy" include, but are not limited to, methoxy, ethoxy, n-propoxy, i-propoxy, t-butoxy, n-butoxy, s-pentoxy and the like. Furthermore, alkoxy groups may be substituted or unsubstituted.

The term "alkenyl" denotes a carbon chain of from 2 to 12, e.g. from 2 to 6, carbon atoms comprising a double bond in its chain. For example, $C_{2-6}$-alkenyl groups, include, e.g., ethenyl, propen-1-yl, propen-2-yl, buten-1-yl, buten-3-yl, penten-1-yl, penten-2-yl, penten-3-yl, penten-4-yl, hexen-1-yl, hexen-2-yl, hexen-3-yl, hexen-4-yl and hexen-5-yl. Furthermore, alkenyl groups may be substituted or unsubstituted.

The term "alkynyl" is intended to include hydrocarbon chains of either linear or branched configuration, having one or more carbon-carbon triple bonds that may occur in any stable point along the chain. Unless otherwise specified, "alkynyl" groups refer refers to groups having 2 to 8, e.g. 2 to 6 carbons. Examples of "alkynyl" include, but are not limited to prop-2-ynyl, but-2-ynyl, but-3-ynyl, pent-2-ynyl, 3-methylpent-4-ynyl, hex-2-ynyl, hex-5-ynyl, etc. Furthermore, alkynyl groups may be substituted or unsubstituted.

The term "cycloalkyl" denotes any stable cyclic or polycyclic hydrocarbon group containing 3 to 13 carbons, e.g., e.g. from 3 to 6 carbons. As in the case of other alkyl moieties, cycloalkyl can optionally be substituted with one or more substituents.

The term "cycloalkenyl" includes any stable cyclic or polycyclic hydrocarbon groups of from 3 to 13 carbon atoms, e.g. 5 to 8 carbon atoms, which contains one or more unsaturated carbon-carbon double bonds that may occur in any point along the cycle. As in the case of other alkenyl moieties, cycloalkenyl may optionally be substituted.

Cycloalkynyl includes any stable cyclic or polycyclic hydrocarbon groups of from 5 to 13 carbon atoms, which contains one or more unsaturated carbon-carbon triple bonds that may occur in any point along the cycle. As in the case of other alkynyl moieties, cycloalkynyl may optionally be substituted.

The term "heterocyclyl" refers to non-aromatic ring systems having five to fourteen ring atoms, e.g. 5 to 10 ring atoms, in which one or more ring carbons, e.g. 1 to 4, are each replaced by a heteroatom such as N, O, or S, the rest of the ring members being carbon atoms. The heterocyclyl can optionally be substituted with one or more substituents, independently at each position.

The term "heteroaryl" refers to a mono- or polycyclic aromatic ring system having 5-14 ring atoms, e.g. 5 or 6 ring atoms, containing at least one ring heteroatom selected from N, O, or S, the rest of the ring members being carbon atoms. Heteroaryl moieties can optionally be substituted, independently at each position. Examples of heteroaryl moieties include but are not limited to those in the molecules disclosed or exemplified herein.

The term "aliphatic group" refers to, e.g., alkyl, alkenyl, alkynyl, alkoxy, haloalkyl, cycloalkyl, cycloalkenyl, cycloalkynyl or non-aromatic heterocyclic groups. Aliphatic groups may contain one or more substituents.

The term "amine" may refer to an organic compound or functional group (i.e. amino) that contains a basic nitrogen atom with a lone electron pair, including, primary amine ($NRH_2$), secondary amine ($NR_1R_2H$), and tertiary amine ($NR_1R_2R_3$) where each R may be the same or different. Also, two R groups may denote members of a ring, e.g., where N is a heteroatom in a heterocyclic or heteroaryl ring.

Also included within the scope of the present disclosure are pharmaceutically acceptable salts the compounds disclosed herein.

The descriptions of compounds of the present application are limited by principles of chemical bonding known to those skilled in the art. Accordingly, where a group may be substituted by one or more substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions.

Pharmaceutical Compositions and Dosage Forms

The radiosensitizer compounds disclosed herein may be present in a pharmaceutical composition, or in one of various pharmaceutical dosage forms, suitable for administration to a subject. Pharmaceutical compositions and dosage forms comprising the radiosensitizer compounds of the present disclosure are useful for enhancing the effects of ionizing radiation.

A "pharmaceutical composition" refers to a combination of ingredients that facilitates administration of one or more agents of interest (e.g. a radiosensitizer compound) to a subject. A pharmaceutical composition generally comprises one or more agents of interest in admixture with one or more pharmaceutically acceptable carriers or diluents. Many pharmaceutically-acceptable "carriers" and "diluents" are known in the art and these generally refer to a pharmaceutically-acceptable materials, compositions, or vehicles, including liquid or solid fillers, diluents, excipients, solvents, binders, or encapsulating materials.

Each component in the composition must be "pharmaceutically acceptable" in the sense of being compatible with the other ingredients of a pharmaceutical formulation. Each component the composition, including the radiosenzitizer compound, must also be "biocompatible", such that the composition is suitable for contact with the tissues or organs of a subject without excessive toxicity, irritation, allergic response, immunogenicity, or other problems or complications, commensurate with a reasonable benefit/risk ratio.

For more information on pharmaceutical compositions, see, e.g., Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004).

The pharmaceutical compositions disclosed herein may be formulated in any suitable dosage form, including single-unit and multiple-unit dosage forms. Exemplary dosage forms include, for example, a liquid, a solution, a suspension, an emulsion, a concentrate, a powder, a paste, a gel, a gum, a drop, a tablet, a capsule or a microcapsule. In some embodiments, the dosage form is a liquid. In some embodiments, the liquid is a solution, a suspension, or an emulsion.

Routes of Administration

The radiosensitizer compounds and pharmaceutical compositions containing them may be administered by any suitable route of administration. For example, the radiosensitizer compound be administered locally (e.g. into a tumor), regionally (e.g. into a body cavity) or systemically (e.g. into a blood vessel, such as a vein or artery).

In some embodiments, the radiosensitizer compound is formulated for enteral administration, topical administration, parenteral administration, or nasal administration. Enteral administration may comprise, for example, oral administration.

In some embodiments, the radiosensitizer compound or composition is formulated for parenteral administration. Parenteral administration may comprise, for example, intravenous, intraarterial, intracerebral, intraperitoneal, intramuscular, subcutaneous, intracardiac, or intraosseous administration. In some embodiments, the parenteral administration is intravenous administration, e.g. injection or infusion. In some embodiments, the parenteral administration is intraarterial administration. In some embodiments, the parenteral administration is intraperitoneal administration.

In some embodiments, the parenteral administration is systemic or regional. In some embodiments, the parenteral administration is systemic. In some embodiments, the radiosensitizer compound or composition is administered intravenously.

Dosage of Radiosenzitizer

The radiosensitizer compound or composition may be administered according to any treatment regimen deemed appropriate by the skilled worker (e.g. clinician).

The dosage requirements of the radiosensitizer compounds and pharmaceutical compositions containing them will vary with the particular combinations employed, the route of administration and the particular cancer and cancer patient being treated. Treatment will generally be initiated with small dosages less than the optimum dose of the compound. Thereafter, the dosage is increased until the optimum effect under the circumstances is reached. In general, the radiosensitizer compounds and compositions according to the present invention are administered at a concentration that will afford effective results without causing any harmful or deleterious side effects. As with any chemo-radiotherapy, a certain degree of toxic side effects may be considered acceptable.

In general, a sufficient amount of the radiosensitizing compound should be employed to effectively react with the particular dose of ionizing radiation employed. Generally, a dose of the radiosensitizing compound will be selected such that the radiosensitizing compound does not contribute significant unwanted effects to the combination.

When administered for the treatment or inhibition of a particular disease state or disorder, the effective dosage of the radiosensitizing compound may vary depending upon the particular compound utilized, the mode of administration, the condition, and severity thereof, of the condition being treated, the dosage of ionizing radiation employed, as well as the various physical factors related to the individual being treated. In many cases, satisfactory results may be obtained when the compound is administered in a daily dosage of between about 0.01 mg/kg and about 500 mg/kg, between about 0.1 mg/kg and about 125 mg/kg, between 1 mg/kg and about 50 mg/kg between 1 mg/kg and about 25 mg/kg, between about 0.3 mg/kg and about 15 mg/kg, or between about 0.5 mg/kg and 5 mg/kg, or between about 5 mg/kg and 10 mg/kg. In some embodiments, the radiosensitizer compounds are substantially non-toxic to normal cells and therefore may be tolerated at relatively high doses (e.g. 10 mg/kg—about 50 mg/kg, or between about 10 mg/kg to about 30 mg/kg). The projected daily dosages are expected to vary with route of administration. Thus, parenteral dosing will often be at levels of roughly 10% to 20% of oral dosing levels.

Radiation Therapy

Radiation therapy, or radiotherapy, is the medical use of ionizing radiation, generally as part of cancer treatment to control or kill malignant cells. Ionizing radiation is radiation composed of particles that individually carry enough kinetic energy to liberate an electron from an atom or molecule thereby ionizing it. Ionizing radiation sources may include external radiation sources, for example, x-radiation (x-rays), gamma-radiation (γ-rays), beta-radiation (β-rays), neutral or charged particle beams, Auger electron sources, internal radiation sources (brachytherapy or sealed source radiation therapy), and radioisotope sources (systemic radioisotope therapy or unsealed source radiotherapy). The radiosensitizer compounds disclosed herein may be used in combination with any suitable source of ionizing radiation that provides electrons capable of reacting with the compounds.

Ionizing radiation may include X-radiation, gamma-radiation, β-radiation, neutral or charged particle radiation, internal radiation (sealed source radiation), Auger electron source, and radioisotope radiation (unsealed source radiotherapy). In some embodiments, the ionising radiation employed will be X-radiation, γ-radiation or β-radiation. In some embodiments, the ionising radiation will be X-radiation. In some embodiments, the ionising radiation will be γ-radiation. In some embodiments, the ionising radiation will be β-radiation. Other forms of DNA damaging factors are also included in the present invention such as UV-irradiation and/or the directed delivery of radiation from a localized internal radiation source (sealed source) or systemic radioisotopes.

Dosage of Ionizing Radiation

The dosages of ionising radiation will be those known for use in clinical radiotherapy. For example, X-rays may be fractionally dosed in daily doses of 1.8-2.0 Gy, 5 days a week for 5-6 weeks. Normally, a total fractionated dose will lie in the range 45-60 Gy. Single larger doses, for example 5-10 Gy may be administered as part of a course of radiotherapy. Single doses may be administered intraoperatively. Hyperfractionated radiotherapy may be used whereby small doses of X-rays are administered regularly over a period of time, for example 0.1 Gy per hour over a number of days. Dosage ranges for radioisotopes vary widely, and depend on the half-life of the isotope, the strength and type of radiation emitted, and on the uptake by cells.

The size of the dose of each therapy which is required for the therapeutic or prophylactic treatment of a particular disease state will necessarily be varied depending on the host treated, the route of administration and the severity of the illness being treated. Accordingly, the optimum dosage may be determined by the practitioner who is treating any particular patient. For example, it may be necessary or desirable to use fractional radiation doses (e.g., 2 Gy/treatment) combined any of the herein mentioned compound doses (e.g., 7 mg/kg/treatment) for multiple treatments (e.g., daily treatments, 5 days a week for 5-6 weeks) in order to achieve the optimal treatment efficacy. In some cases, the doses may be reduced in a combination therapy.

Combination Therapy

It is demonstrated herein that contacting cancer cells with a non-platinum-based radiosensitizer compound of the disclosure in combination with ionizing radiation in vitro or in vivo provides an enhanced efficacy of radiotherapy, i.e. synergy, while the compound itself is substantially non-toxic within the usable doses. Furthermore, its combination with ionizing radiation induces no radiation toxicity (i.e, independent of radiation dose). The radiosensitizer compounds disclosed herein therefore provide a novel combination therapy for disorders treatable by radiation therapy, such as cancer. The combination therapy is thus a chemo-radiotherapy combination that includes a radiosensitizing compound as disclosed herein and ionizing radiation.

As used herein, the term "combination therapy" means that, at some point during the treatment, the two components of the combination will interact, in particular, at a target site(s). The target site may, for example, be the site of a cancer cell or a tumor. The two or more components of the combination therapy are not necessarily administered together at the same time. The radiosensitizing compound and the ionizing radiation may, for example, be administered simultaneously (e.g. at substantially the same time), sequentially (e.g. staggered times), or at overlapping intervals.

In some embodiments, the radiosensitizer compound and the ionizing radiation are administered simultaneously (e.g. together at the same time, or within about 30 seconds of each other). In some embodiments, radiosensitizer compound and the ionizing radiation are administered in sequence. In some embodiments, the radiosensitizer compound and the ionizing radiation are administered sequentially, e.g. within 1 minute, 2 minutes, 5 minutes, 10 minutes, 20 minutes, 30 minutes, 40 minutes, 50 minutes, 1 hour, 1.5 hours, 2 hours, 3 hours, 5 hours, or more, of each other.

In some embodiments, the radiosensitizer compound is administered before the ionizing radiation, for example, to give the compound sufficient time to reach the target site before applying the radiation. In some embodiments, the radiosensitizer compound is administered about 10 minutes to about 2 hours before the ionizing radiation. In some embodiments, the radiosensitizer compound is administered after the ionizing radiation. In some embodiments, the radiosensitizer compound is administered about 1 minute to about 5 hours after the ionizing radiation.

A skilled person can determine the appropriate timing, which will depend on such factors as absorption rate, bioavailability, and half-life.

Methods of Treatment

The combination therapies disclosed herein are typically administered to individuals who have been diagnosed with cancer. However, in some cases, the combination therapy may be administered to individuals who do not yet show clinical signs of cancer, but who are at risk of developing cancer. Toward this end, the present application also discloses methods for preventing or reducing the risk of developing cancer. The combination therapies disclosed herein may also be used to treat a relapse or to prolong a remission. The combination therapies disclosed herein may also be used to treat other disorders treatable by radiation therapy, including non-malignant conditions, such as trigeminal neuralgia, acoustic neuromas, severe thyroid eye disease, pterygium, pigmented villonodular synovitis, and prevention of keloid scar growth, vascular restenosis, and heterotopic ossification.

In one aspect, the present disclosure relates to methods of enhancing radiation therapy. In some embodiments, the method of enhancing radiotherapy in a subject in need thereof comprises administering an effective amount of a radiosensitizer compound as defined herein to the subject in combination with an effective amount of ionizing radiation.

In another aspect, the present disclosure provides a method of providing an anti-cancer effect in a cancer cell, comprising: a) administering to the cancer cell an effective amount of a compound as defined herein; and b) administering to the cancer cell an effective amount of ionizing radiation, wherein a) and b) are administered sequentially or simultaneously to thereby provide the anti-cancer effect. In some embodiments, the anti-cancer effect is killing of the cancer cell. In some embodiments, the cancer cell is a tumor cell.

In one aspect, the present disclosure provides a method of treating cancer in a subject in need thereof comprising: a) administering to the subject an effective amount of a compound as defined herein; and b) administering to the subject an effective amount of ionizing radiation, wherein a) and b) are administered sequentially or simultaneously.

In some embodiments, the compound is administered before, during or after administration of the ionizing radiation. In some embodiments, the compound is administered before or during administration of the ionizing radiation. In some embodiments, the compound is administered before administration of the ionizing radiation.

In one aspect, the present disclosure provides a method of treating cancer in a subject in need thereof comprising, administering to the subject a therapeutically effective amount of a radiosensitizer compound as defined herein before or simultaneously with an effective amount of ionizing radiation.

In preferred embodiments, the combinations of the present disclosure have a net anticancer effect that is greater than the anticancer effect of the individual components of the combination when administered alone. Thus, in another aspect, the present disclosure provides a synergistic combination of a radiosensitizer compound as disclosed herein and ionizing radiation. Preferably, the anticancer effect is increased without a concomitant increase in toxic side effects.

In another aspect, there is provided a synergistic combination of a radiosensitizer compound as defined herein and ionizing radiation for the treatment of cancer. Also provided is a synergistic combination comprising a radiosensitizer compound as defined herein for use in the manufacture of a medicament for in use in combination with ionizing radiation for the treatment of cancer.

In another aspect the method comprises administering to a subject in need thereof a therapeutically effective amount of a compound highly reactive with a prehydrated electron. In preferred targeting and radical formation and reaction, the agent is capable of showing an anticancer effect under ionizing radiation and no systemic and radiation-induced toxic effects. The combination is administered in a therapeutically effective amount. The features of the combination are as described in any of the embodiments disclosed herein above.

In another aspect, there is provided a method of overcoming cisplatin resistance, wherein any of the methods described above are applied to a cell or a cancer that is resistant to cisplatin treatment, or are applied to a subject having a cell or a cancer that is resistant to cisplatin treatment.

It is to be understood that the terminology used herein is for the purpose of describing specific embodiments only and is not intended to be limiting. It is further to be understood that unless specifically defined herein, the terminology used herein is to be given its common meaning as known to skilled persons in the relevant field.

The term "subject" as used herein refers to a human or an animal to be treated, in particular, a mammal. Mammalian animals may include, for example, primate, cow, sheep, goat, horse, dog, cat, rabbit, rat, or mouse. In some embodiments, the subject is a human, although the compounds disclosed herein are useful in vertinary applications as well. The terms "subject" and "patient" may be used interchangeably.

The term "cancer" (e.g. neoplastic disorder) as used herein refers to a disorder involving aberrant cell growth, proliferation or division (e.g. neoplasia). As cancer cells grow and divide they pass on their genetic mutations and proliferative characteristics to progeny cells. A "tumour" (e.g. neoplasm) is an accumulation of cancer cells. The methods and combinations disclosed herein may be used in the treatment of cancer, cancer cells, tumors and/or symptoms associated therewith.

Exemplary types of cancer that may be treated in accordance with the methods, uses and combinations of the present disclosure include, but are not limited to, testicular cancer, bladder cancer, cervical cancer, ovarian cancer, breast cancer, prostate cancer, head cancer, neck cancer, lung cancer (e.g. non small cell lung cancer), endometrial cancer, pancreatic cancer, Kaposi's sarcoma, adrenal cancer, leukemia, stomach cancer, colon cancer, rectal cancer, liver cancer, esophageal cancer, renal cancer, thyroid cancer, uterine cancer, skin cancer, oral cancer, brain cancer, spinal cord cancer, liver cancer, gallbladder cancer. The cancer may, for example, include sarcoma, carcinoma, melanoma, lymphoma, myeloma, or germ cell tumours. In some embodiments, the cancer is testicular cancer, bladder cancer, cervical cancer, ovarian cancer, breast cancer, prostate cancer, head cancer, neck cancer, or lung cancer (e.g. non small cell lung cancer).

An "anti-cancer agent" refers to a therapeutic agent that directly or indirectly kills cancer cells, for example, by triggering apoptosis, or directly or indirectly prevents, stops or reduces the proliferation of cancer cells. In some cases, an "anti-antineoplastic agent" may include more than one therapeutic agent.

The terms "treat," "treating" and "treatment" include the eradication, removal, amelioration, modification, reduction, management or control of a tumor, tumor cells or cancer, the minimization, prevention or delay of metastasis, or the prolongation of survival of the subject.

The term "metastasis," as used herein, refers to the dissemination of tumor cells via lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

The term "effective amount" or "therapeutically effective amount" is intended to mean that amount of a therapeutic component, or components in a combination therapy, that will elicit a desired biological or medical response in a cell, tissue, tumor, system, or subject, which result is generally sought by a researcher, veterinarian, doctor or other clinician or technician. When referring to the effective amount of a radiosensitizing compound to be administered in combination with ionizing radiation, the effective amount of the may be an amount sufficient to provide a desired anti-cancer effect in the presence of the ionizing radiation. Similarly, when referring to the effective amount of ionizing radiation to be administered in combination with a radiosensitizing compound, the effective amount may be an amount of ionizing radiation sufficient to provide a desired anti-cancer effect in the presence of the compound. Advantageously, the effective amount of one or both components may be lower when the components are combined.

Synergistic combinations are particularly desirable. In some embodiments, the combination exhibits a synergistic anti-cancer effect. The terms "synergistic" and "synergy" imply that the effect of the combined components of the combination is greater than the sum of the effects of the individual components when administered alone.

An "anticancer effect" may include, but is not limited to, reduction, prevention or elimination of cancer cells, a tumor, or cancer; reduced or inhibited cancer cell proliferation; increased or enhanced killing or apoptosis of cancer cells; reduction or prevention of metastasis, and/or prolonged survival of a subject. In some cases, a desired biological or medical response may be amelioration, alleviation, lessening, or removing of one or more symptoms of cancer, or reduction in one or more toxic side effects associated with a particular cancer treatment.

By "inhibiting" or "reducing", e.g. cancer cell proliferation, it is generally meant to slow down, to decrease, or, for example, to stop the amount of cell proliferation, as measured using methods known to those of ordinary skill in the art, by, for example, 10%, 20%, 30%, 40%, 50%, 60%, 70%, 80%, 90%, 95%, or 100%, when compared to proliferating cells that are either not treated or are not subjected to the methods and combinations of the present application.

By "reducing" a tumor it is generally meant to reduce the size of a tumour, as measured using methods known to those of ordinary skill in the art, by, for example, 10%, 20%, 30%, 40%, 50%, 60%, 70%, 80%, 90%, 95%, or 100%, when compared to tumor size before treatment or compared to tumors that are not subjected to the methods and combinations of the present application.

By "increased" or "enhanced" killing or apoptosis of cancer cells, it is generally meant an increase in the number of dead or apoptotic cells, as measured using methods known to those of ordinary skill in the art, by, for example, 10%, 20%, 30%, 40%, 50%, 60%, 70%, 80%, 90%, 95%, 100%, 200%, 300% or more, when compared to cells that are either not treated or are not subjected to the methods and combinations of the present application. An increase in cell killing or apoptosis could also be measured as a decrease in cell viability, as measured using a standard cell viability assay.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

As used herein, the singular forms "a", "an", and "the" include plural references unless indicated otherwise.

Terms of degree such as "substantially", "about" and "approximately", as used herein, mean a reasonable amount of deviation of the modified term such that the end result is not significantly changed. These terms of degree should be construed as including a deviation of at least ±5% of the modified term if this deviation would not negate the meaning of the word it modifies.

Adjunct Therapy

The combination therapy disclosed herein may be administered as a sole therapy or may be used in conjunction with one or more additional therapies, such as surgery or drug therapy. For instance, the additional therapy may be a cancer therapy including surgery, e.g. to remove a primary tumor, or a therapeutic agent, e.g., an antibiotic, anti-inflammatory agent or anticancer agent. Anticancer agents may include, for example, classic chemotherapeutic agents, as well as molecular targeted therapeutic agents, biologic therapy agents, and radiotherapeutic agents. Anticancer agents used in further combination with the combination therapy of present disclosure may include agents selected from any of the classes known to those of ordinary skill in the art, including, for example, alkylating agents, anti-metabolites, plant alkaloids and terpenoids (e.g., taxanes), topoisomerase inhibitors, anti-tumor antibiotics, hormonal therapies, molecular targeted agents, and the like. Generally such an anticancer agent is an alkylating agent, an antimetabolite, a vinca alkaloid, a taxane, a topoisomerase inhibitor, an anti-tumor antibiotic, a tyrosine kinase inhibitor, or an immunosuppressive macrolide. It will be understood that the additional agents selected should not significantly interfere with the combination therapy of the present disclosure so as to significantly reduce effectiveness of the combination therapy or enhance unwanted toxic side effects.

Uses

The radiosensitizing compounds disclosed herein are useful in combination with ionizing radiation, e.g. for enhancing radiotherapy.

Thus, in one aspect, there are provided radiosensitizer compounds as defined herein for enhancing the effects of radiation therapy in a subject receiving said radiation therapy. In another aspect, there are provided radiosensitizer compounds as defined herein for use in the treatment of cancer in a subject receiving radiation therapy. In another aspect, there are provided radiosensitizer compounds as defined herein for use in combination with radiation therapy in the treatment of cancer. In another aspect, there are provided radiosensitizer compounds as defined herein for use in the manufacture of a medicament for the treatment of cancer in a subject receiving radiation therapy. In another aspect, there are provided radiosensitizer compounds as defined herein for use in the manufacture of a medicament for use in combination with radiation therapy the treatment of cancer.

In another aspect, there is provided a use of a radiosensitizer compound as defined herein to enhance radiation therapy in a subject receiving said radiation therapy. In another aspect, there is provided a use of a radiosensitizer compound as defined herein in the treatment of cancer in a subject receiving radiation therapy. In another aspect, there is provided a use of a radiosensitizer compound as defined herein in the manufacture of a medicament for the treatment of cancer in a subject receiving radiation therapy.

In some embodiments described above, the subject has a cancer that is resistant to cisplatin treatment.

In a accordance with the use, the combination is for administration in a therapeutically effective amount. The features of the use are as described in any of the embodiments disclosed herein above.

Kits and Commercial Packages

In another aspect, there are provided kits and commercial packages related to the radiosensitizer compounds as disclosed herein for use in combination with ionizing radiation. In some embodiments, a kit or commercial package is provided comprising a radiosensitizer compound as disclosed herein, together with instructions for use in combination with ionizing radiation. In some embodiments, the instructions are for use in combination with ionizing radiation in the treatment of cancer.

Dissociative Electron Transfer (DET) Reaction

The present inventor recently deduced the molecular mechanism of action of cisplatin in combination with radiotherapy [Lu 2007; 2010]. Although cisplatin is a well-known DNA-attacking agent, its precise molecular mechanism of action had remained elusive until recently solved [Lu 2007]. Through the use of femtosecond time-resolved laser spectroscopy (fs-TRLS), it was demonstrated that cisplatin is a very effective molecule for the dissociative-electron transfer (DET) reaction with a weakly-bound prehydrated electron ($e_{pre}^-$) generated in radiotherapy:

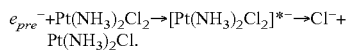

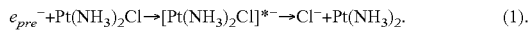

The resultant cis-Pt(NH$_3$)$_2$ radical highly effectively leads to DNA strand breaks [Lu, 2007].

The present inventor has now discovered that certain non-platinum-based organic molecules can also participate in the DET reaction with a weakly-bound prehydrated electron ($e_{pre}^-$) generated in radiotherapy, essentially acting as cisplatin analogues. Some general features of the radiosensitizing compounds of the present disclosure are that they comprise an aromatic ring (rather than a platinum coordinating ion), coupled to one or more electron transfer promoters, such as NH$_2$ groups, and one or more leaving groups, such as halogen. Such compounds are demonstrated herein to be effective radiosensitizing compounds.

Advantageously, such compounds are also demonstrated herein to be significantly less toxic to normal cells than cisplatin. In fact, the examples provided herein demonstrate that the exemplary compounds are substantially non-toxic to normal cells, even at high doses.

It is demonstrated herein that contacting cancer cells with a non-platinum-based radiosensitizer compound of the disclosure in combination with ionizing radiation in vitro or in vivo provides an enhanced efficacy of radiotherapy, i.e. synergy, while the compound itself is substantially non-toxic within the usable doses. Furthermore, its combination with ionizing radiation induces no radiation toxicity (i.e, independent of radiation dose).

Based on the deduced dissociative-electron-transfer (DET) mechanism of cisplatin, described above, the non-platinum-based radiosensitizer compound (RSC) is believed to react with a prehydrated electron ($e_{pre}^-$) via a DET reaction as follows:

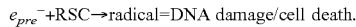

The resultant radical can effectively lead to DNA damage and cell death, e.g. DNA damage and cell death in a cancer cell or tumor.

Studies were carried out to explore the in vitro and in vivo anti-tumor effects of the above compounds in combination with ionizing radiation. Some of the results are discussed below.

FS-TRLS Study of Radiosensitizer Compounds (RSCs)

The reactivity of a RSC with the prehydrated electron ($e_{pre}^-$) was studied by fs-TRLS measurements, as outline in Example 1. FIG. 2 shows that the DET reaction of compound D as an exemplary RSC is indeed much more effective than that of IdU. The latter has previously been tested as a potential radiosensitizer but failed in Phase III clinical trials [Prados et al., 1999]. This suggests that the present disclosed RSCs are more promising than IdU as a radiosensitizing agent for radiotherapy of cancer.

DNA Damage Study of Radiosensitizer Compounds (RSCs)

The damage to plasmid DNA in pure water and with the presence of Compound B under ionizing radiation (X-ray irradiation) was studied by agarose gel electrophoresis, as outlined in Example 2. FIGS. 3 and 4 show that radiation-induced DNA damage, the yield of double-strand breaks (DSBs), was significantly enhanced by the presence of Compound B. DSBs are particularly lethal to cells.

In Vitro Toxicity Tests of Radiosensitizer Compounds (RSCs)

The in vitro toxicity of cisplatin or RSCs alone was investigated in human (skin) normal cells (GM05757), as outlined in Example 3. The GM05757 cell line has been widely used as human normal cells in cancer research, particularly in testing new radiosensitizing agents [Choudhury et al. 2009]. FIG. 5 shows that the normal cells were effectively killed by cisplatin in a dose-dependent manner with a measured IC50 of about 10 µM (at which the cell survival rate is 50% with respect to untreated cells), confirming that cisplatin is indeed highly toxic. In contrast, the results plotted in FIGS. 6-9 show that the present disclosed RSCs, Compounds A, B, C and D, had essentially no toxicity toward the normal cells in doses up to 200 µM. Thus, these RSCs are expected to induce few or no toxic side effects, in contrast to the heavy-metal (Pt)-based chemotherapeutic drug (cisplatin) in human patients. The viability of cells was measured by MTT assay, one of the most commonly used cell viability assays. This method involves the conversion of MTT (3-(4,5-dimethylthiazol-2-yl)-2,5-diphenyltetrazolium bromide) to an insoluble formazan by metabolically-active cells (live cells). Using a solubilizing agent, the formazan is dissolved and its absorbance measured, giving indication to the number of cells that survive. This is a well-established quantitative method that is rapid in terms of the required drug treatment time as well as the total protocol time compared to the clonogenic assay, which measures cell survival on the long-term scale.

In Vitro Radiation-Toxicity Tests of Radiosensitizers (RSCs)

The in vitro toxicity of cisplatin or RSCs in combination with ionizing radiation (x-rays) was investigated in human normal cells (GM05757), as outlined in Example 4. FIG. 10 shows cell survival rates of human normal cells (GM05757) after the 12-hr treatment of cisplatin with various concentrations, followed by 0-10 Gy 225 keV X-ray irradiation. The viability of cells in 96-well plates was measured by MTT at 12 days after irradiation. This result shows that the normal cell viability was independent of radiation dose. This confirms that in spite of being highly toxic as a chemotherapeutic drug, cisplatin induced essentially no radiation toxicity. Therefore cisplatin has been used as a radiosensitizer in the clinic [Rose et al., 1999]. Interestingly, FIGS. 11-13 show a similar observation for RSCs, which exhibited no toxicity induced by ionizing radiation. These results indicate that the disclosed RSCs can potentially be used as radiosensitizing agents for radiotherapy of cancer.

In Vitro Radiosensitivity Effect Tests of New Radiosensitizers (RSCs)

The in vitro radiosensitizing effects of RSCs in combination with ionizing radiation (x-rays) were investigated in cisplatin sensitive human cervical cancer cell line (HeLa or ME-180), cisplatin-resistant human ovarian cancer (NIH: OVCAR-3, HTB-161) and human lung cancer (A549) cell lines, as outlined in Example 5. FIG. 14-21 show cell survival rate of various human cancer cells after the treatment of a RSC with various concentrations for 12 hr, followed by various doses of 225 keV X-ray irradiation. These results show that Compounds A, B, C and D enhanced the killing of cancer cells in a radiation dose dependent manner and in synergy with radiation. Significant enhancements in the radiosensitivity of cancer cells to X-ray by RSCs were clearly observed. For example, about 20% cancer cells (ME-180) survived after 50 Gy x-ray irradiation without the presence of any RSC, while early all cancer cells were killed at 50 Gy with the presence of about 100 µM Compound B or D, which showed no toxicity against human normal cells.

The in vitro results presented herein demonstrate that the presence of a RSC enhances the effectiveness of ionizing radiation to kill tumor cells but no normal cells. Thus, the RSCs are expected to enhance the efficacy of radiotherapy while induce minimal or no toxic side effects in human cancer patients.

In Vivo Toxicity Studies of RSCs

The overall drug toxicity was studied in 6-8 week SCID mice through a survival assay and body weight measurements, and the acute drug toxicity was measured through the following parameters: blood collection and histology, as outlined in Example 6. The hepatotoxicity (ALT, ALP, AST), nephrotoxicity (blood BUN, creatinine), and electrolytes (Na, K, etc) were analyzed by HPLC-mass spectroscopy. For cisplatin as a clinically used radiosensitizer, it was reported that cisplatin was administered by intraperitoneal (IP) injection in mice once per week at a typical dose of about 10 mg/kg in the literature, which is below the LD50 (=13.5 mg/kg) of cisplatin. In the present studies, Compound B as an exemplary RSC was intentionally administered by IP injection into mice at 0, 5 and 7 mg/kg daily for 10 days due to the non-toxicity observed in vitro cell line experiments. Mice were observed for any physical toxicity. At the end of the study, whole organs were harvested in order to assess gut, liver, and kidney toxicity. Blood was also collected. FIG. 22 shows that the survival rate of mice was 100%, that is, Compound B was non-toxic and had no impact on mice survival. FIG. 23 also shows that there was no effect on the weight of mice with time, i.e., Compound B exhibited no physical toxicity. Moreover, the results plotted in FIGS. 24-26 show that Compound B even given at the highest dose (10 day×7 mg/kg/day=70 mg/kg) induced no observable acute toxicity, i.e., no hepatotoxicity, no nephrotoxicity, and no changes in electrolytes.

In Vivo Pharmacokinetics (PK) & Pharmacodynamics (PD) Studies of RSCs

The pharmacokinetics (PK) & pharmacodynamics (PD) of a representative RSC, compound B in SCID mice was studied, as outlined in Example 7. Blood samples were collected from the saphenous vein of mice at various time points after IP injection of the compound into the mice at 0-7 mg/kg and then analyzed using HPLC-Mass Spectrometry. First, significant levels of compound B in the blood were detected. Second, FIG. 27 shows that the highest concentration of compound B was observed at about 20 minutes after i.p. injection and dropped to nearly zero at about 3 hr. Although it is expected that it would take a longer time for compound B to reach a maximum concentration at the (tumor) tissue. The observed result in FIG. 27 shows that compound B can be well expelled from the body within a few hours, indicating that Compound B has excellent pharmacokinetics & pharmacodynamics.

In Vivo Radiosensitizing Effects of RSCs

The in vivo radiosensitizing (e.g. anticancer) effects of a combination of Compound B and X-ray irradiation were investigated in the xenograft mouse tumor model of human cervical cancer (ME-180), as outlined in Example 8. The combination of Compound B with x-ray irradiation significantly enhanced the suppression of tumor growth, compared with the treatments of radiation or Compound only in the tumor model, as can be seen from the tumor (volume) growth curves shown in FIG. 28, photos of tumor growths in FIG. 29 and tumor volumes and MRI images shown in FIG. 30. All of these results show that the combination of Compound B with ionizing radiation resulted in a significant shrinkage of the tumor in mice. Given that only a single dose (7 mg/kg) of compound B and a single radiation dose of 15 Gy used and that Compound B has minimal overall and acute toxicity, it is predicted that these results can be extrapolated to multiple fractional radiotherapy (e.g., 5 fractional doses with 7 mg/kg and 4 Gy per fractional treatment) so that a maximal synergistic effect in enhancing the therapeutic effect can be achieved.

It is believed that the in vitro and in vivo results from the Examples provided herein can be extrapolated to other combinations, cancer cells, cancer models and human cancers beyond those exemplified. With the information provided herein, a rational approach can be used to identify other new radiosensitizers besides those exemplified herein that can be used in combination with ionizing radiation to enhance its anticancer effect. Various screening assays known to those skilled in the art can be used to assess the effect of a particular combination, as can the in vitro and in vivo experiments set forth in the Examples. Those combinations demonstrating synergy will be particularly preferred, as well as those that do not result in a net increase in toxic side effects compared to treatment with the radiotherapy (ionizing radiation) alone. This rational approach to identifying effective compounds and combinations represents an efficient and economical alternative to random screening assays.

Since some of the exemplary compounds tested herein already exist, the radiosensitizing agents disclosed herein represent synergistic combination treatments for cancer that can be easily moved forward into the clinical setting. Skilled professionals will readily be able to determine the effective amounts required for the chemo-radiotherapy in vivo, e.g. so as to achieve the desired anticancer effect while having minimal toxic side effects. Effective dosages may vary depending on the type and stage of cancer, the route of administration, the treatment regimen, among other factors. Studies can furthermore be conducted by skilled professionals in order to determine the optimal drug dose and radiation dose to be combined.

One advantage of the RSCs disclosed herein is that the disclosed DET reaction mechanism is designed to be preferentially active at tumor cells. In contrast to normal cells, where a RSC will have a low affinity, thus the DET will not occur or its reaction efficiency will be significantly lowered in normal tissue. Thus the disclosed compounds will make a naturally targeted radiotherapy of multiple types of cancers, including (but not limited to) as cervical, ovarian, breast, lung, prostate, brain and spinal cord, head and neck, and colorectal cancers.

Some desired characteristics of the RSCs include one or a combination of the following: (1) biocompatible; (2) effective reaction with weakly-bound electrons ($e_{pre}^-$); (3) enhance the radiosensitivity of cancer cells so that lower radiation doses can be used; (4) minimal toxicity (ideally, substantially non-toxic) at doses to be administered; (5) reactive in a hypoxic tumor environment; (6) preferentially reactive with cancer cells; (7) capable of entering a cell and preferably nucleus; and/or (8) applicable to multiple types of tumors.

Applying the principles disclosed herein, persons of skill in the art will be able to identify radiosensitizing compounds that can enhance the effect of radiotherapy. Thus, the scope of the present disclosure extends beyond the exemplary compounds and combinations disclosed.

A number of theories, hypotheses, beliefs and postulations are discussed herein. Such theories, hypotheses, beliefs and postulations are not intended to be binding or to limit the scope of the disclosure.

EXAMPLES

The examples set forth below are intended to illustrate but not limit the scope of the disclosure.

Example 1

Femtosecond Laser Spectroscopic Observation of the DET Reaction of Radiosensitizer Compounds (RSCs) with $e_{pre}^-$ 1.1 fs-TRLS Method Femtosecond (fs) time-resolved laser spectroscopy (fs-TRLS) is the most versatile and powerful technique for real-time observation of molecular reactions. It uses laser flashes of such short duration that we are down to the time scale on which the reactions actually happen—femtoseconds (fs) (1 fs=$10^{-15}$ seconds). The DET reactions of new radiosensitizers with $e_{pre}^-$ were studied by fs-TRLS [Lu, 2007; 2010]. For the latter, briefly our fs laser amplifier system (Spectra-Physics, Spitfire) produced laser pulses with a pulse width of 100-120 fs at a repetition rate of 500 Hz. A intense pump pulse at 322 nm was used to simulate ionizing radiation by 2-photon excitation of a $H_2O$ molecule into a higher energy state $H_2O^*$ that then ionizes to produce an $e_{pre}^-$; a probe pulse at 333 nm coming at certain delay was used to monitor the DET reaction with $e_{pre}^-$ by detecting transient anion absorbance.

1.2 Results

A representative fs-TRLS observation of the DEA reaction of new radiosensitizers (e.g., Compound D) is shown in FIG. 2. The results show that the DET reaction of compound D with $e_{pre}^-$ was much stronger than that of iododeoxyuridine (IdU). The latter has the strongest DET reaction among the halopyrimidines [Lu, 2010]. This observation illustrates that the disclosed compounds are potent radiosensitizers.

1.3 Discussion

The presence of (mono- or di-)halogen and diamino groups in the disclosed compounds can indeed enhance the DET reactions of with $e_{pre}^-$ that is a major radical produced in the radiolysis of water under ionizing radiation.

Example 2

Gel Electrophoresis Measurements of DNA Damage Induced by New Radiosensitizers 2.1 Materials and Method.

Ultrapure water for life science with a resistivity of >18.2 MΩ/cm and TOC<1 ppm obtained freshly from a Barnstead Nanopure water system was used. Dibromo-diamino-benzene (Dibromo-phenylenediamine, Compound B) was obtained from TCI-America, while other chemicals and buffer compositions were obtained from Sigma-Aldrich. Plasmid DNA [pGEM 3Zf(−), 3197 kbp] was extracted from *Escherichia Coli* JM 109 and purified using QIAprep Kit (Qiagen).

Agarose Gel Electrophoresis.

The pump beam at 322 nm, identical to that for fs-TRLS measurements, was used to produce radicals via two-photon excitation of water in DNA solutions. The laser beam was focused into a quartz cell containing 3.0 μg of DNA in 200 μL of buffer solutions. The solutions were stirred during irradiation to produce uniform DNA damage throughout the samples. Aliquots equivalent to 96 ng DNA were removed from the sample cell in various irradiation times for gel electrophoresis. All aliquots were analyzed with a standard agarose gel electrophoresis method, namely, on 1% neutral TAE agarose gel in TAE running buffer. The gel was prestained with 0.5 μg/ml ethidium bromide. The image of the gel was taken on a FluorChem imaging station (Alpha Innotech) and exhibits various DNA topological forms, including closed-circular supercoiled (SC, undamaged DNA), open circular (C, SSB) and linear form (L, DSB). They were quantified with an AlphaEase FC software.

2.2 Results

As shown in FIGS. 3 and 4, the disclosed compounds indeed resulted in DNA double-strand breaks. The disclosed compounds have high efficacy in causing DNA damage.

2.3 Discussion

Owing to the strong DET reactions with $e_{pre}^-$ that is a major radical produced in the radiolysis of water under ionizing radiation, the disclosed compounds consisting of (mono- or di-)halogen and diamino groups indeed enhanced their efficacy in inducing DNA damage.

Example 3

In Vitro Tests on the Toxicity of RSCs in Treating Human Normal Cells 3.1 Materials & Methods 3.1.1 Chemicals and Reagents Cisplatin, dichloro-diamino-benzene (Compound A), bromo-diamino-benzene (Compound D), insulin, and 3-(4, 5-Dimethylthiazol-2-yl)-2,5-diphenyltetrazolium bromide (MTT) were obtained from Sigma-Aldrich. Dibromo-diamino-benzene (Dibromo-phenylenediamine, Compound B) was obtained from TCI-America. Diiodo-diaminobenzene (Compound C) were synthesized, purified and crystallized in our laboratory, and the structures and purity were examined by NMR and mass spectrometry. MEM and fetal bovine serum (FBS), penicillin G and streptomycin were obtained from Hyclone Laboratories (UT, USA). Stock solution of cisplatin was freshly prepared in ultrapure water or saline, and stock solutions of Compounds A, B, C, D were prepared in pure ethanol, where the final concentration of ethanol was ≤1% when treated to cells.

3.1.2 Cell Culture

A human skin diploid fibroblast (GM05757 cell line) was obtained from the Coriell Cell Repository directly. Fetal bovine serum (FBS) was obtained from Hyclone Laboratories (UT, USA). The GM05757 normal cells were cultivated with MEM (Hyclone) supplemented with 10% FBS, 100 units/mL penicillin G and 100 μg/mL streptomycin (Hyclone). The cells were maintained at 37° C. in a humidified atmosphere containing 5% $CO_2$.

3.1.3 Cell Survival Measurement by MTT

The radiosensitizing effects of RSCs on cell viability were determined by the 3-[4,5-dimethylthiazol-2-yl]-2,5-diphenyl tetrazoliumbromide (MTT) assay. Cells were cultured in 96-well plates ($5\times10^3$ cells/well) for 24 h. The culture medium was replaced by fresh culture medium and incubated for 72 h with varying drug concentrations. The MTT assay of cell viability was then conducted. Briefly, 100 μl new medium without phenol red containing 1.2 mM MTT (sigma) (i.e., adding 10 μl 12 mM MTT stock solution in PBS) were added to each well and incubated for 4 h. The medium was then removed, and the formazan crystals solubilized by 100 μL/well DMSO (or alternatively by 100 μl/well SDS and incubated for another 4 h). The surviving fraction was determined by measuring the absorbance at 540 nm (570 nm for SDS solubilization) using a Multiskan Spectrum UV/Vis microplate reader (Thermo Scientific), which is directly proportional to the number of viable cells.

3.2 Results

To test the toxicity of RSCs on human normal cells, the standard MTT assay was utilized and cisplatin was used as a reference. Human normal (GM05757) cells were treated with various drug concentrations (0-50 μM for cisplatin and 0-200 μM for compound A/B/C/D). The results are shown in FIGS. 5-9. First, it is clearly seen in FIG. 5 that cisplatin exhibits severe toxicity even at low concentrations of ≤30 μM with a measured IC50 of about 10 μM. This result confirms that cisplatin as an anti-cancer agent is indeed a highly toxic. In contrast, it is clearly demonstrated in FIGS. 6-9 that the present disclosed RSCs, Compounds A, B, C and D, have essentially no toxicity toward the normal cells even at very high concentration of 200 μM. These results demonstrate the contrast difference between the heavy-metal (Pt)-based chemotherapeutic drug (cisplatin) and RSCs. Thus, these RSC molecules are expected to induce no or minimal systematic toxic side effects in animals and human patients.

3.3 Discussion

As the present inventor hypothesized, normal cells due to the lack of a reductive intracellular environment have a low affinity to the disclosed compounds that are highly oxidizing. Therefore, the RSCs show no or low toxicity towards normal cells. The disclosed compounds are in contrast to the clinically used cisplatin which has a high affinity to human normal cells and is highly toxic. Thus, these RSCs have the potential to be excellent anticancer agents.

Example 4

In Vitro Tests on the Radiation-Induced Toxicity of RSCs in Treating Human Normal Cells 4.1 Materials & Methods 4.1.1 Chemicals and Reagents Cisplatin, dichloro-diamino-benzene (Compound A), bromo-diamino-benzene (Compound D), insulin, and 3-(4, 5-Dimethylthiazol-2-yl)-2,5-diphenyltetrazolium bromide (MTT) were obtained from Sigma-Aldrich. Dibromo-di-amino-benzene (Dibromo-phenylenediamine, Compound B) was obtained from TCI-America. Diiodo-diaminobenzene (Compound C) were synthesized, purified and crystallized in our laboratory, and the structures and purity were examined by NMR and mass spectrometry. MEM and fetal bovine serum (FBS), penicillin G and streptomycin were obtained from Hyclone Laboratories (UT, USA). Stock solution of cisplatin was freshly prepared in ultrapure water or saline, and stock solutions of Compounds A, B, C, D were prepared in pure ethanol, where the final concentration of ethanol was ≤1% when treated to cells.

4.1.2 Cell Culture

A human skin diploid fibroblast (GM05757 cell line) was obtained from the Coriell Cell Repository directly. Fetal bovine serum (FBS) was obtained from Hyclone Laboratories (UT, USA). The GM05757 normal cells were cultivated with MEM (Hyclone) supplemented with 10% FBS, 100 units/mL penicillin G and 100 μg/mL streptomycin (Hyclone). The cells were maintained at 37° C. in a humidified atmosphere containing 5% $CO_2$.

4.1.3 Cell Survival Measurement by MTT

The radiosensitizing effects of RSCs on cell viability were determined by the 3-[4,5-dimethylthiazol-2-yl]-2,5-diphenyl tetrazoliumbromide (MTT) assay. Cells were cultured in 96-well plates ($5\times10^3$ cells/well) for 24 h. The culture medium was replaced by fresh culture medium and incubated for 12 h with varying drug concentrations. The cells were then irradiated by 225 kV X-ray (PRECISION X-RAD IR 225) at a dose rate of 2 Gy/min with various X-ray doses. After irradiation, the cells were incubated for 12 days. The MTT assay of cell viability was then conducted. Briefly, 100 μl new medium without phenol red containing 1.2 mM MTT (sigma) (i.e., adding 10 μl 12 mM MTT stock solution in PBS) were added to each well and incubated for 4 h. The medium was then removed, and the formazan crystals solubilized by 100 μL/well DMSO (or alternatively by 100 μl/well SDS and incubated for another 4 h). The surviving fraction was determined by measuring the absorbance at 540 nm (570 nm for SDS solubilization) using a Multiskan Spectrum UV/Vis microplate reader (Thermo Scientific), which is directly proportional to the number of viable cells.

4.2 Results

The in vitro toxicity of cisplatin and RSCs in combination with ionizing radiation (x-rays) was investigated in human normal cells (GM05757). FIG. 10 shows cell survival rates of human normal cells (GM05757) after the 12-hr treatment of cisplatin with various concentrations, followed by 0-10 Gy 225 keV X-ray irradiation. The viability of cells in 96-well plates was measured by MTT at 12 days after irradiation. This result shows that the normal cell viability was independent of radiation dose. This confirms that in spite of being highly toxic as a chemotherapeutic drug, cisplatin induced essentially no radiation toxicity. Therefore cisplatin has been used as a radiosensitizer in the clinic [Rose et al., 1999]. Interestingly, FIGS. 11-13 show a similar observation for RSCs, that is, no toxicity induced by combination with ionizing radiation was observed. These results indicate that like cisplatin, the disclosed RSCs can potentially be used as radiosensitizing agents for radiotherapy of cancer in the clinic.

4.3 Discussion

As mentioned above, the disclosed RSCs have a low affinity to normal cells and therefore a low toxicity with and without the presence of ionizing radiation.

Example 5

In Vitro Radiosensitizing Results of RSCs in Treating Various Cancer Cells 5.1 Materials & Methods 5.1.1 Chemicals and Reagents Cisplatin, dichloro-diamino-benzene (Compound A), bromo-diamino-benzene (Compound D), insulin, and 3-(4,5-Dimethylthiazol-2-yl)-2,5-diphenyltetrazolium bromide (MTT) were obtained from Sigma-Aldrich. Dibromo-diamino-benzene (Dibromo-phenylenediamine, Compound B) was obtained from TCI—America. Diiodo-diaminobenzene (Compound C) were synthesized, purified and crystallized in our laboratory, and the structures and purity were examined by NMR and mass spectrometry. MEM and fetal bovine serum (FBS), penicillin G and streptomycin were obtained from Hyclone Laboratories (UT, USA). Stock solution of cisplatin was freshly prepared in ultrapure water or saline, and stock solutions of Compounds A, B, C, D were prepared in pure ethanol, where the final concentration of ethanol was ≤1% when treated to cells.

5.1.2 Cell Culture

A human skin diploid fibroblast (GM05757 cell line) was obtained from the Coriell Cell Repository directly, while the human cervical cancer cell line (HeLa, ATCC#: CCL-2; or ME-180), human ovarian cancer cell line (NIH:OVCAR-3, ATCC#: HTB-161) and human lung cancer cell line (A549, ATCC#: CCL-185™), together with RPMI 1640, F-12K, McCoy's 5 A and L-15 culture media, were obtained from the American Type Culture Collection (ATCC) directly. Fetal bovine serum (FBS) was obtained from Hyclone Laboratories (UT, USA). The GM05757 normal cells and HeLa cells were cultivated with MEM (Hyclone) supplemented with 10% FBS, 100 units/mL penicillin G and 100 μg/mL streptomycin (Hyclone). The complete growth media for ME-180, NIH:OVCAR-3, A549 and MDA-MB-231 cells were the ATCC-formulated McCoy's 5 A Medium supplemented with 10% FBS, RPMI 1640 medium with 20%, F-12K medium with 10% FBS, and L-15 Medium (Leibovitz) with 10% FBS, respectively. The cells were maintained at 37° C. in a humidified atmosphere containing 5% $CO_2$.

5.1.3 Cell Survival Measurement by MTT

The radiosensitizing effects of RSCs on cell viability were determined by the 3-[4,5-dimethylthiazol-2-yl]-2,5-diphenyl tetrazoliumbromide (MTT) assay. Cells were cultured in 96-well plates ($5 \times 10^3$ cells/well) for 24 h. The culture medium was replaced by fresh culture medium and incubated for 12 h with varying drug concentrations. The cells were then irradiated by 225 kV X-ray (PRECISION X-RAD IR 225) at a dose rate of 2 Gy/min with various X-ray doses. After irradiation, the cells were incubated for 6 days. The MTT assay of cell viability was then conducted. Briefly, 100 μl new medium without phenol red containing 1.2 mM MTT (sigma) (i.e., adding 10 μl 12 mM MTT stock solution in PBS) were added to each well and incubated for 4 h. The medium was then removed, and the formazan crystals solubilized by 100 μL/well DMSO (or alternatively by 100 μl/well SDS and incubated for another 4 h). The surviving fraction was determined by measuring the absorbance at 540 nm (570 nm for SDS solubilization) using a Multiskan Spectrum UV/Vis microplate reader (Thermo Scientific), which is directly proportional to the number of viable cells.

5.2 Results

The in vitro radiosensitizing effects of RSCs in combination with ionizing radiation (x-rays) were investigated in cisplatin sensitive human cervical cancer cell line (HeLa or ME-180), cisplatin-resistant human ovarian cancer (NIH:OVCAR-3, HTB-161) and human lung cancer (A549) cell lines. FIG. 14-21 show cell survival rate of various human cancer cells after the treatment of a RSC with various concentrations for 12 hr, followed by various doses of 225 keV X-ray irradiation. These results show that Compounds A, B, C and D enhanced the killing of cancer cells in a radiation dose dependent manner and in synergy with radiation, in striking contrast to the results for human normal cells (FIGS. 11-13). It is clearly seen that the radiosensitivity of cancer cells to X-ray was significantly enhanced by the presence of RSCs. For example, about 20% cancer cells (ME-180) survived after 50 Gy x-ray irradiation without the presence of any RSC, while early all cancer cells were killed at 50 Gy with the presence of about 100 μM Compound B or D, which showed no toxicity against human normal cells.

5.3 Discussion

The in vitro results presented herein demonstrate that the presence of a RSC (Compound A/B/C/D) enhances the effectiveness of ionizing radiation to kill tumor cells but no normal cells. Thus, the RSCs are expected to enhance the efficacy of radiotherapy while induce minimal or no toxic side effects in human cancer patients.

Example 6

In Vivo Test on the Toxicity of Compound B in SCID Mice 6.1 Materials and Protocol 6.1.1 Study Groups The three groups (five 6-8 week SCID mice/group) in the experiment were: (1) control article (5% EtOH/medium); (2) Compound B 5 mg/kg in 5% EtOH/medium; and (3) Compound B 7 mg/kg in 5% EtOH/medium, as shown in Table 1. Compound B was injected IP every day for 10 days.

TABLE 1

Study Groups in Example 6

| Group # | Group Name | No. mice | TA/CA* Dose (mg/kg) | Admin. Route | Volume (μL/20 g) | Schedule (Days) |
|---|---|---|---|---|---|---|
| 1 | Control (vehicle) | 5 | N/A | i.p. | 200 | Daily for 10 days |
| 2 | Compound B | 5 | 5 | i.p. | 200 | Daily for 10 days |
| 3 | Compound B | 5 | 7 | i.p. | 200 | Daily for 10 days |

*TA: Test Article; CA: Control Article 6.1.2 Mouse and Compound B Solution Preparation:

6-8 week SCID mice were used in this study; Compound B as an exemplary RSC was dissolved in 5% EtOH: 95% (cell culture) medium (≈1:20).

6.1.3 Dose Administration 6-8 week SCID Mice were individually weighed and injected intraperitoneally (IP) according to body weight for an injection concentration as outlined in the study group table above. Compound B was administered by IP injection into mice at 0, 5 and 7 mg/kg daily for 10 days. The injection volume was based on 200 μL per 20 g mouse. The skin surface was wiped down with 70% isopropyl alcohol to clean the injection site.

6.1.4 Data Collection and Analysis

The overall drug toxicity in mice was observed by a survival assay and body weight measurements, and the acute drug toxicity was measured by blood collection and histology. The hepatotoxicity (ALT, ALP, AST), nephrotoxicity (blood BUN, creatinine), and electrolytes (Na, K, etc) were analyzed by HPLC-mass spectroscopy. Mice were observed for any physical toxicity. Blood samples were collected from the saphenous vein at various time points after drug injection. At the end of the study, whole organs were harvested in order to assess gut, liver, and kidney toxicity.

6.1.5 Evaluation of Drug Induced Stress in the Mice

All animals were observed post administration, and at least once a day, more if deemed necessary, during the pre-treatment and treatment periods for mortality and morbidity. In particular, animals were monitored for signs of ill health such as body weight loss, change in appetite, behavior changes such as altered gait, lethargy and gross manifestations of stress.

6.2 Results

The overall drug toxicity was studied in 6-8 week SCID mice through a survival assay and body weight measurements, and the acute drug toxicity was studied by measurements of the hepatotoxicity (ALT, ALP, AST), nephrotoxicity (blood BUN, creatinine), and electrolytes (Na, K, etc). As shown in FIG. 22, the survival rate of mice was 100%, that is, Compound B exhibited non-toxicity and had no impact on mice survival. It is also clearly seen in FIG. 23 that Compound B showed no effect on the weight of mice with time, exhibiting no physical toxicity. Interestingly, it is also clearly shown in FIGS. 24-26 that Compound B even given at an unusually high dose (10 day×7 mg/kg/day=70 mg/kg), which is approximately 10 times the dose of cisplatin used in mouse experiments and humans, induced no observable acute toxicity, i.e., no hepatotoxicity, no nephrotoxicity, and no changes in electrolytes in mice.

6.3 Discussion

The in vivo results presented in FIGS. 22-26 have clearly demonstrated the exciting observation that Compound B exhibits no or minimal toxicity in mice, no overall drug toxicity (no effects on mouse survival and body weight) and no acute toxicity (no hepatotoxicity, no nephrotoxicity, and no changes in electrolytes). These results are in excellent agreement with the in vitro results observed in human normal cells (shown in FIGS. 6-9). It is therefore proven that Compound B as a RSC is non-toxic indeed.

Example 7

In Vivo Pharmacokinetics (pk) & Pharmacodynamics (pd) Studies of Compound B in Mice 7.1 Materials and Method 7.1.1 Data Collection and Analysis Blood samples were collected from the saphenous vein of mice at various time points after IP injection of the compound into the mice and then analyzed using HPLC-Mass Spectrometry.

7.2 Results

The pharmacokinetics (PK) & pharmacodynamics (PD) of compound B as an exemplary RSC in SCID mice was studied. First, significant levels of compound B in the blood were detected. Second, it is clearly shown in FIG. 27 that the highest concentration of compound B was observed at about 20 minutes after i.p. injection and dropped to nearly zero at about 3 hr. Although it is expected that it would take a longer time for compound B to reach a maximum concentration at the (tumor) tissue. The observed result shows that compound B can be well expelled from the body within a few hours, indicating that Compound B has excellent pharmacokinetics & pharmacodynamics.

Example 8

In Vivo Test of Compound B in the Xenograft Mouse Model of Human Cervical Cancer (ME-180) in Female SCID Mice 8.1 Materials and Protocol 8.1.1 Study Groups The four groups in the experiment were: (1) control article (5% EtOH/medium); (2) 15 Gy X-ray irradiation; (3) Compound B at 7 mg/kg in 5% EtOH/medium and (4) Compound B at 7 mg/kg in 5% EtOH/medium plus 15 Gy X-ray irradiation, as shown in Table 2.

TABLE 2

Study Groups in Example 8

| Group # | Group Name | No. mice | Drug/ Radiation Dose | Admin. Route | Volume (µL/20 g) | Schedule |
|---|---|---|---|---|---|---|
| 1 | Control | 5 | N/A | N/A | N/A | Day 1 |
| 2 | X-ray irradiation | 5 | 15 Gy | i.p. | N/A | Day 1 |
| 3 | Compound B | 5 | 7 mg/kg | i.p. | 200 | Day 1 |
| 4 | Compound B + X-ray irradiation | 5 | 7 mg/kg + 15 Gy | i.p. | 200 | 1 hr prior to x-ray irradiation |

8.1.2. Cell Preparation (Harvesting for s.c. Inoculation):

ME-180 (human cervical cancer) cells were cultured in the ATCC-formulated McCoy's 5 A Medium supplemented with 10% FBS. The cells in a flask were maintained at 37° C. in a humidified atmosphere containing 5% $CO_2$. The cells were rinsed with PBS, trypsined for detachment from the bottom of the flask, mixed with fresh growth medium, and centrifuged to remove the supernatant. The cells were re-suspend with fresh medium to appropriate concentration for inoculation. Injection volume was 50 µl ($1 \times 10^6$ cells) per animal.

8.1.3 Tumour Cell Implantation (Solid Tumours)

ME-180 tumour cells were implanted subcutaneously into female SCID mice (age 6-8 weeks) in a volume of 50 µL into the left gastrocneumius muscle using a 27-gauge needle. This was established as a subcutaneous (SC) xenograft mouse model of human cervical cancer.

8.1.4 Drug and Radiation Dose Administration

Mice were individually weighed and injected intraperitoneally according to body weight for an injection concentration as outlined in the study group table above. The injection volume was based on 200 µL per 20 g mouse. The skin surface was wiped down with 70% isopropyl alcohol to clean the injection site. Radiation was given using X-rad 225 targeted irradiator to the tumors.

8.1.5 Data Collection

Tumor size was measured as a function of time to assess tumor growth delay associated with treatment using slide caliper and micro MM. Animals were also weighed at the time of tumour measurement. Tumours in mice were allowed to grow to a maximum of 1000 $mm^3$ before termination.

8.1.6 Evaluation of Drug Induced Stress in the Mice

All animals were observed post administration, and at least once a day, more if deemed necessary, during the pre-treatment and treatment periods for mortality and morbidity. In particular, animals were monitored for signs of ill health such as body weight loss, change in appetite, behaviour changes such as altered gait, lethargy and gross manifestations of stress.

8.2 Results

The in vivo radiosensitizing (e.g. anticancer) effects of a combination of Compound B and X-ray irradiation were investigated in the xenograft mouse tumor model of human cervical cancer (ME-180). As shown in FIG. 28-30, it is clearly seen the combination of Compound B with x-ray irradiation significantly enhanced the suppression of tumor growth, compared with the treatments of radiation or Compound only in the tumor model. The results show that compound B in combination with ionizing radiation resulted in a very significant tumor growth delay in vivo till 21 days. Given that only a single dose (7 mg/kg) of compound B and a single radiation dose of 15 Gy used in the present experiment and that Compound B has the observed no or minimal overall and acute toxicity, it is reasonably expected that these results can be extrapolated to multiple fractional radiotherapy (e.g., 5 fractional doses with 5×7 mg/kg and 5×4 Gy for the whole treatment course could be applied) so that a maximal synergistic effect in enhancing the therapeutic effect could be achieved.

No signs of toxicity or ill health, neither overall drug toxicity (no effects on mouse survival and body weight), nor acute toxicity (no hepatotoxicity, no nephrotoxicity, and no changes in electrolytes), were noted in any of the animals treated.

The references recited herein are incorporated by reference in their entirety.

The above-described embodiments are intended to be examples only. Alterations, modifications and variations can be effected to the particular embodiments by those of skill in the art without departing from the scope of the disclosure, which is defined solely by the claims appended hereto.

REFERENCES

1. P. G. Rose, B. N. Bundy, E. B. Watkins, J. T. Thigpen, G. Deppe, M. A. Maiman, D. L. Clarke-Pearson, S. Insalaco. Concurrent cisplatin-based radiotherapy and chemotherapy for locally advanced cervical cancer. N. Engl. J. Med. 340, 1144-53(1999).
2. D. M. Reese, Anticancer drugs, Nature 378, 532(1995).
3. Q. B. Lu, US/WO Patent (WO/2011/026219), "Novel Combination Therapy of Cisplatin with Non-Toxic Molecular Promoters (Compounds) for Cancer Treatment".
4. Q.-B. Lu, Molecular Reaction Mechanisms of Combination Treatments of Low-Dose Cisplatin with Radiotherapy and Photodynamic Therapy, J. Med. Chem. 50, 2601-2604(2007).
5. Q.-B. Lu, Effects of Ultrashort-Lived Prehydrated Electrons in Radiation Biology and Their Applications for Radiotherapy of Cancer, Mutat. Res.-Rev. Mutat. Res. 704, 190-199(2010).
6. M. D. Prados et al. "A phase 3 randomized study of radiotherapy plus procarbazine, CCNU, and vincristine (PCV) with or without BUdR for the treatment of anaplastic astrocytoma: a preliminary report of RTOG 9404", Int. J. Radiat. Oncol. Biol. Phys. 45, 1109(1999).
7. A. Choudhury et al., Targeting homologous recombination using imatinib results in enhanced tumor cell chemosensitivity and radiosensitivity, Mol Cancer Ther 8, 203-2013 (2009).

The invention claimed is:

1. A method of treating cancer in a patient comprising administering to said patient a biocompatible radiosensitizer compound in combination with ionizing radiation, wherein the compound is selected from the group consisting of:

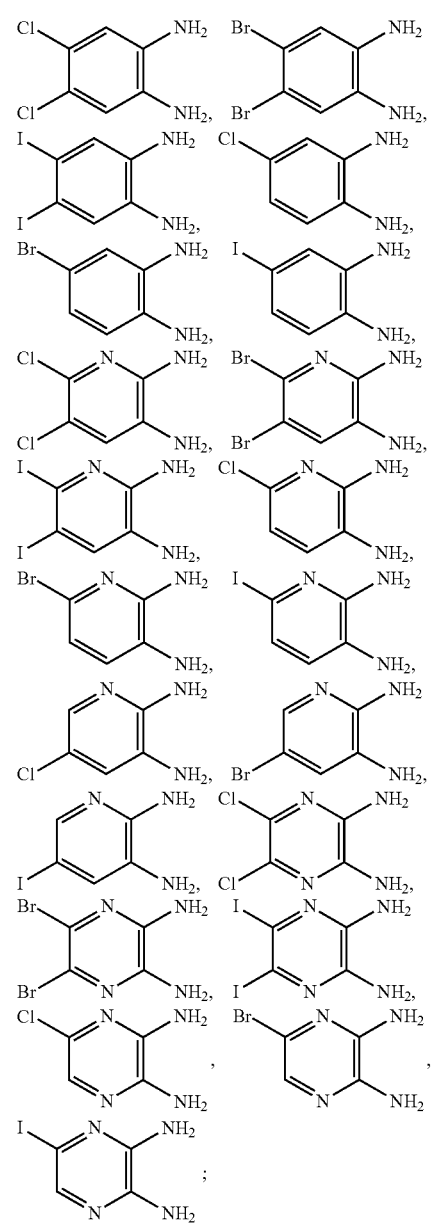

and a pharmaceutically acceptable salt thereof.

2. The method of claim 1, wherein the compound and the ionizing radiation are administered sequentially or simultaneously.

3. The method of claim 1, wherein the compound is radiolabelled.

4. The method of claim 3, wherein compound is radiolabelled with one or more atoms selected from the group consisting of $^3$H, $^{14}$C, $^{32}$P, $^{35}$S, $^{43}$F and $^{36}$Cl.

5. The method of claim 1, wherein the compound is formulated for enteral administration.

6. The method of claim 5, wherein the compound is formulated for oral administration.

7. The method of claim 1, wherein the compound is administered parenterally.

8. The method of claim 7, wherein the compound is formulated for intravenous, intramuscular, or subcutaneous administration.

9. The method of claim 7, wherein the compound is administered intravenously.

10. The method of claim 7, wherein the compound is administered systemically.

11. The method of claim 7, wherein the compound is administered regionally.

12. The method of claim 1, wherein the subject is administered a pharmaceutical formulation comprising an effective amount of the compound and one or more pharmaceutically acceptable carriers or diluents.

13. The method of claim 1, wherein the ionizing radiation is external source radiation.

14. The method of claim 13, wherein the ionizing radiation is X-ray radiation.

15. The method of claim 13, wherein the ionizing radiation is gamma ($\gamma$)-ray radiation.

16. The method of claim 13, wherein the radiation is neutral or charged particle radiation.

17. The method of claim 16, wherein the ionizing radiation is $\beta$-ray radiation.

18. The method of claim 1, wherein the ionizing radiation is internal radiation sources.

19. The method of claim 1, wherein the ionizing radiation is radioisotope sources.

20. The method of claim 1, wherein the combination therapy of the compound with ionizing radiation further includes one or more additional cancer therapies.

* * * * *